(12) United States Patent
Trudsoe

(10) Patent No.: US 8,293,285 B2
(45) Date of Patent: Oct. 23, 2012

(54) CARRAGEENAN MODIFIED BY ION-EXCHANGE PROCESS

(75) Inventor: Jens Eskil Trudsoe, Roskilde (DK)

(73) Assignee: CP Kelco U.S., Inc., Atlanta, GA (US)

( * ) Notice: Subject to any disclaimer, the term of this patent is extended or adjusted under 35 U.S.C. 154(b) by 118 days.

(21) Appl. No.: 12/403,097

(22) Filed: Mar. 12, 2009

(65) Prior Publication Data

US 2011/0008470 A1    Jan. 13, 2011

Related U.S. Application Data

(60) Provisional application No. 61/207,856, filed on Mar. 14, 2008, provisional application No. 61/207,858, filed on Mar. 14, 2008, provisional application No. 61/207,857, filed on Mar. 14, 2008.

(51) Int. Cl.
  *A01N 59/00* (2006.01)
  *A23C 9/14* (2006.01)

(52) U.S. Cl. ........................ 424/722; 426/271

(58) Field of Classification Search .............. 424/722; 426/271
  See application file for complete search history.

(56) References Cited

U.S. PATENT DOCUMENTS

| | | | |
|---|---|---|---|
| 742,124 | A | 10/1903 | Martin et al. |
| 2,011,594 | A | 8/1935 | Seltzer et al. |
| 2,516,023 | A | 7/1950 | Siehrs et al. |
| 3,094,517 | A | 6/1963 | Stanley |
| 3,907,770 | A | 9/1975 | Strong |
| 3,956,173 | A | 5/1976 | Towle |
| 4,414,236 | A | 11/1983 | Moran et al. |
| 5,002,934 | A | 3/1991 | Norton et al. |
| 5,502,179 | A * | 3/1996 | Larsen .................. 536/114 |
| 5,741,482 | A | 4/1998 | Modi |
| 5,777,102 | A | 7/1998 | Larsen |
| 5,801,240 | A | 9/1998 | Rideout et al. |
| 6,063,915 | A | 5/2000 | Hansen et al. |
| 2004/0063927 | A1 | 4/2004 | Tsai et al. |
| 2004/0129174 | A1 | 7/2004 | Li et al. |
| 2005/0020828 | A1 | 1/2005 | Therkelsen |
| 2005/0070702 | A1 * | 3/2005 | Therkelsen ................ 536/54 |
| 2005/0106233 | A1 | 5/2005 | Andersen et al. |
| 2005/0171083 | A1 | 8/2005 | Magnusson et al. |
| 2007/0281065 | A1 * | 12/2007 | Modliszewski et al. ...... 426/575 |
| 2008/0317683 | A1 | 12/2008 | Trudso |
| 2008/0317789 | A1 | 12/2008 | Trudso |
| 2008/0317790 | A1 | 12/2008 | Trudsoe |
| 2008/0317791 | A1 | 12/2008 | Trudsoe |
| 2008/0317926 | A1 | 12/2008 | Trudsoe |
| 2008/0317927 | A1 | 12/2008 | Trudso |

FOREIGN PATENT DOCUMENTS

| | | |
|---|---|---|
| EP | 0355908 | 2/1990 |
| EP | 0465373 A2 | 8/1992 |

OTHER PUBLICATIONS

Written Opinion and International Preliminary Report on Patentability, PCT/US2008/066832, International Searching Authority, Jan. 5, 2010.
Written Opinion and International Preliminary Report on Patentability, PCT/US2008/067610, International Searching Authority, Jan. 5, 2010.
Written Opinion and International Preliminary Report on Patentability, PCT/US2008/067261, International Searching Authority, Jan. 5, 2010.
Disclosure Under 37 CFR 1.56, dated Jan. 6, 2011, for U.S. Appl. No. 12/403,097.
International Search Report for PCT/US09/37047, Apr. 20, 2009.
Written Opinion and International Preliminary Report on Patentability, PCT/US2009/037047, International Searching Authority.
Disclosure Under 37 CFR 1.56, dated Nov. 3, 2010, for U.S. Appl. No. 12/403,097.
U.S. Statutory Invention Registration No. H2050, Santos et al., Oct. 1, 2002.
Disclosure Under 37 CFR 1.56,. dated Jul. 29, 2011, for U.S. Appl. No. 12/403,097.

* cited by examiner

*Primary Examiner* — Fereydoun G Sajjadi
*Assistant Examiner* — Genevieve S Alley
(74) *Attorney, Agent, or Firm* — Sutherland Asbill & Brennan LLP

(57) ABSTRACT

A composition comprises an ion-exchanged carrageenan. The carrageenan may be a traditionally extracted or neutrally extracted iota or kappa carrageenan. The ion-exchanged carrageenan has reduced gelling cation contents, reduced gelling temperature, and reduced melting temperature, as compared to its non-ion-exchanged counterpart. The ion-exchanged carrageenan may be mixed with another carrageenan to form a carrageenan product having a unique gelling temperature and melting temperature. Also disclosed is a process for making an ion-exchanged carrageenan composition.

10 Claims, 16 Drawing Sheets

US 8,293,285 B2

CARRAGEENAN MODIFIED BY ION-EXCHANGE PROCESS

The present application claims the benefit of priority of U.S. Provisional Patent Application No. 61/207,856, filed Mar. 14, 2008, entitled "Ion Exchange Resin Process for Use with Carrageenan"; and U.S. Provisional Patent Application No. 61/207,858, filed Mar. 14, 2008, entitled "Kappa Carrageenan Products and Methods for Making"; and U.S. Provisional Patent Application No. 61/207,857, filed Mar. 14, 2008, entitled "Carrageenan Process and Apparatus"; the disclosures of which are incorporated herein by reference in their entirety.

FIELD

The present invention relates to carrageenan compositions and processes for making such. More specifically, the present invention relates to iota or kappa carrageenan compositions with reduced gelling cations and processes that result in reducing gelling cations in carrageenan extracts.

BACKGROUND

Production of carrageenan can be traced back to Ireland where plants of the red seaweed algae species of *chondrus crispus* were first harvested with rakes during low tide or by gathering seaweed that had washed ashore. After harvesting, the weeds were typically washed, sun-bleached, dried and boiled with milk to form a pudding. The weeds themselves were dubbed "Irish Moss" and after making it familiar to most of Europe, Nineteenth Century Irish immigrants carried it to the U.S. and Canada as well.

Today, this seaweed pudding is mostly confined to Ireland's cultural history, but carrageenan has become much more important because of its effectiveness as a functional food additive in forming gels in an aqueous system, which make it useful in a wide variety of applications, including beer (in which it has been used for over 150 years as a fining) to processed meat and food products like milk drinks and deserts; pharmaceutical preparations such as orally-administered gel caps; personal care products such as toothpaste and skin care preparations; and household products such as air-freshener gel and cleaning gels.

Contemporary methods of carrageenan extraction and production have advanced considerably in the last fifty years. Perhaps most significantly is that today, rather than being gathered from wild-grown seaweed, carrageenan-containing plants such as *Kappaphycus cottonii* (*Kappaphycus alvarezii*), *Euchema spinosum* (*Euchema denticulatum*), and the above mentioned *Chondrus crispus* are more commonly seeded along nylon ropes and harvested in massive aquaculture farming operations particularly in parts of the Mediterranean and throughout much of the Indian Ocean and along the Asian Pacific Ocean Coastline. Just as in the Nineteenth-century process, in contemporary processes before further processing the seaweed raw materials are first thoroughly cleaned in water to remove impurities and then dried. Then, as described in U.S. Pat. No. 3,094,517 to Stanley et al. (the disclosure of which is incorporated herein by reference) the carrageenan is extracted from the cleaned seaweed while also at the same time being subjected to alkali modification by placing the seaweed in solution made slightly alkaline by the addition of a low concentration of alkali salt (i.e., a pH of the solution is raised to a range of, e.g., 9-10) and then heating this solution to a temperature of around 80° C. for a period of time of about 20 minutes to as long as two hours.

The temperature at which carrageenan gels and melts is dependent on a number of factors that include especially the concentration of gelling cations such as potassium and calcium ions. Generally speaking, the higher the concentration of gelling cations the higher the gelling and melting temperature of the carrageenan. Such cations may come not only from the composition to which the carrageenan is added as a gelling agent, but also from the carrageenan itself.

Carrageenan products with relatively high gelling cation concentrations require relatively high-temperature processing. Generally, lower temperature processes are preferred since these save processing time, are less expensive and don't negatively affect the preparation of the composition in which the carrageenan is being included. Lower temperature processing is especially important for food compositions, where higher temperatures may impair the base foodstuffs that are included in the food product.

Subjecting the carrageenan-containing seaweed to alkali modification has the desired result of reducing the gelling cation concentration in the resulting carrageenan product; however, the extent to which the gelling cation levels can be reduced is limited because only relatively low concentrations of alkali may be used so as to not depolymerise (and thus damage) the carrageenan in the seaweed. So even though the gelling cation concentrations are reduced, they still remain high.

For example, when an alkali modification process is NOT used (viz., in a neutral extraction process), typical cation concentration levels in iota or kappa carrageenan are:

|  | Iota | Kappa |
| --- | --- | --- |
| Potassium: | About 4% | About 4% |
| Calcium: | About 0.6% | About 0.4% |
| Magnesium: | About 0.7% | About 0.5% |
| Sodium: | About 3% | About 2% |

When an alkali modification step is used to reduce these gelling cation concentrations, (viz., in a traditional extraction process), such as in U.S. Pat. No. 3,094,517, which makes use of calcium hydroxide as alkali modification agent, the resulting cation concentration levels in iota or kappa carrageenan are:

|  | Iota | Kappa |
| --- | --- | --- |
| Potassium: | About 5% | About 5% |
| Calcium: | About 3% | About 2% |
| Magnesium: | About 0.1% | About 0.01% |
| Sodium: | About 2% | About 1% |

As can be seen, the alkali modification step taught in U.S. Pat. No. 3,094,517 significantly reduced the levels of magnesium and sodium ions, but not other gelling cations such as potassium and calcium.

By contrast, when other alkalis, such as sodium hydroxide or sodium bicarbonate are used as in U.S. Pat. No. 6,063,915, typical cation levels in iota carrageenan are:

| Potassium: | About 5% |
| --- | --- |
| Calcium: | About 0.05% |
| Magnesium: | About 0.01% |
| Sodium: | About 5% |

SUMMARY

In view of the foregoing there is a need in the art for a process for reducing the concentration of gelling cations, and thereby lowering the gelling and melting temperatures, without depolymerising the carrageenan or damaging it in some other way. Additionally, there is a need for a process that would allow a manufacture to precisely control the melting and gelling temperatures of carrageenan material produced by a manufacturing process.

In accordance with an embodiment, a composition comprises an iota carrageenan that has been subjected to an ion exchange process. The ion-exchanged iota carrageenan has: a potassium content of about 6 mg/g to about 35 mg/g carrageenan; a calcium content of less than about 13 mg/g carrageenan; and a magnesium content of less than about 5 mg/g carrageenan.

In accordance with another embodiment, a composition comprises a traditionally-extracted kappa carrageenan that has been subjected to an ion exchange process. The ion-exchanged kappa carrageenan has a potassium content of about 5 mg/g to about 30 mg/g carrageenan; a calcium content of less than about 7 mg/g carrageenan; and a magnesium content of less than about 0.2 mg/g carrageenan.

In accordance with another embodiment, a composition comprises a neutrally-extracted kappa carrageenan that has been subjected to an ion exchange process. The ion-exchanged kappa carrageenan has: a potassium content of about 4 mg/g to about 30 mg/g carrageenan; a calcium content of less than about 3 mg/g carrageenan; and a magnesium content of less than about 3 mg/g carrageenan.

In accordance with another embodiment, the ion-exchanged carrageenans may be used in a personal care product, a food product, a household product, or a pharmaceutical product.

In accordance with yet another embodiment, a process for producing an ion-exchanged carrageenan composition includes the following steps: (a) extracting a carrageenan starting material with an aqueous treatment solution to form an iota or kappa carrageenan extract; and (b) contacting the carrageenan extract with an acidic cationic ion-exchange material and reducing the cation content of the carrageenan extract to produce an ion-exchanged carrageenan extract.

In accordance with yet another embodiment a process for producing an ion-exchanged carrageenan composition includes the following steps: (a) providing a first carrageenan extract having a first gelling temperature and a first melting temperature; (b) providing a second ion-exchanged carrageenan extract having a second gelling temperature that is different from the first gelling temperature and a second melting temperature that is different from the first melting temperature; and (c) mixing the first carrageenan extract and the second ion-exchanged carrageenan extract to form a third carrageenan product having a third gelling temperature that is between the first and second gelling temperatures; and a third melting temperature that is between the first and second melting temperatures.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE EXEMPLARY EMBODIMENTS

Figure 1:
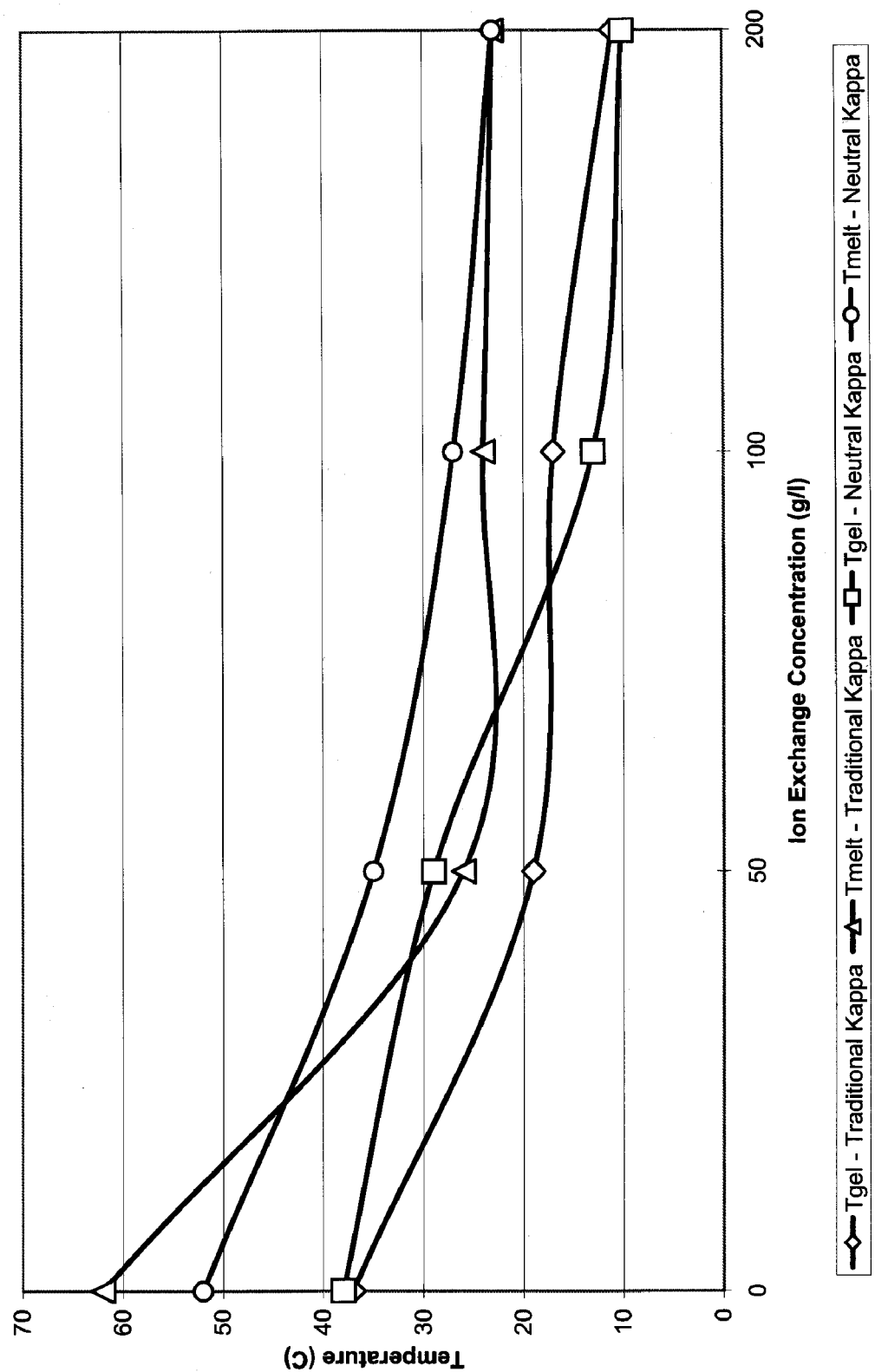
FIG. 1 shows the effect of ion exchange material concentration on the gelling and melting temperatures of kappa carrageenan.

All parts, percentages and ratios used herein are expressed by weight unless otherwise specified. All documents cited herein are incorporated by reference.

By "alkali" it is meant a base according to the Brønsted-Lowry definition, i.e., an alkali is a molecule or ion that accepts a proton in a proton-transfer reaction.

By "solution" it is meant any combination of two or more substances, in the form of, for example without intending to be limiting, a heterogeneous mixture, a suspension, a mixture, a sol, a gel, a dispersion, or an emulsion.

By "traditional," "traditionally extracted," or "traditionally treated" carrageenan it is meant a carrageenan that is subjected to an alkali modification by being contacted with an alkali solution at elevated temperature during processing.

By "neutral," "neutral extracted," or "neutrally treated" carrageenan it is meant a carrageenan that is not contacted with an alkali solution during processing.

The various exemplary embodiments describe herein are directed to carrageenan products, and more specifically iota and kappa carrageenans. Carrageenans may be more specifically described as generic repeating galactose and 3,6-anhydrogalactose residues linked b-(1-4) and a-(1-3), respectively and with characteristic 4-linked 3,6-anhydro-a-D-galactose and 3-linked-b-D-galactose-4-sulphate groups. Kappa carrageenan differs from iota carrageenan only by the presence of a single sulphate group. The molecules arrange themselves in a right-handed double helix with the strands parallel and threefold, again iota and kappa carrageenan are very similar in this regard, with kappa carrageenan forming a slightly more disordered helix. The helix is stabilized by interchain hydrogen bonds through the only unsubstituted positions at O-2 and O-6 with the sulphate groups projecting outward from the helix.

As mentioned above, there is a strong correlation between the presence of gelling cations and gelation. Without being limited by theory, it is believed that gels are formed in carrageenan through gelling (primarily monovalent) cations such as Na, K, Rb, Cs, $NH_4$, $Ca^{2+}$ as well as some divalent cations like calcium atoms that facilitate side-by-side interaction of the strands to form a three dimensional gel network. The exact transformation mechanism from the carrageenan as randomly-oriented coils at higher temperatures to a gelled network is the subject of some dispute. As the temperature is lowered the random coils of carrageenan molecules reaggregate to form gels. In one model of gelation, a gel is created by the formation of the carrageenan molecules into double helices; in certain forms of carrageenan (such as kappa carrageenan) these double helices may themselves aggregate side-by-side due to the influence of the aforementioned gelling cations forming aggregates of double helices and eventually even forming domains of a three-dimensional ordered gel network. Alternatively it has been suggested that upon cooling the random coils of the carrageenan molecules do not form double helices but only single helix structures, and that these single helix structures form single helices in which the gelling cations nested in the bends of the helix promote intermolecular aggregation.

According to various exemplary embodiments a process for making a carrageenan composition includes contacting the extract of carrageenan-containing seaweed with an ion-exchange resin to reduce the amount of gelling cations in the carrageenan. The exemplary embodiments relates specifically to kappa and iota carrageenan, but may be applied to a broader range of carrageenan materials as well.

According to the exemplary embodiments, the carrageenan may be extracted from a carrageenan-containing material. Carrageenan containing materials include, for example, red seaweed. Carrageenan may be extracted from the carrageenan-containing material according to known and later-developed techniques. For example, the carrageenan may be extracted in a completely alkali modified, or partly alkali modified process (i.e., "traditionally treated"), or in a process that is not alkali modified, such as where the seaweed is extracted under neutral conditions (i.e., "neutrally treated"). In an alkali modified or a partly alkali modified process the carrageenan is contacted by an alkali such as sodium hydroxide, and its corresponding carbonates and bicarbonates, typically dissolved in water as an aqueous treatment solution. No such treatment compounds—but only water—are applied in neutrally treated processes. Suitable techniques for extraction are discussed in U.S. Pat. Nos. 3,094,517, 3,907,770 and U.S. Patent Application Publication No. 2008-0317927, the disclosures of which are incorporated herein by reference in their entirety.

In exemplary embodiments, the carrageenan extracts provided by the above traditional treated or neutral treated extraction process contain various levels of gelling cations. The gelling cations include, for example, potassium, calcium, magnesium, and sodium. In one exemplary embodiment, traditional iota carrageenan extract may contain about 50 mg/g K, about 21 mg/g Ca, about 3 mg/g Mg, and about 25 mg/g Na. The content of cations is expressed here as mg/g, which as used herein refers to milligrams of cation per gram of carrageenan. In another exemplary embodiment, neutral iota carrageenan extract may contain about 54 mg/g K, about 6 mg/g Ca, about 7 mg/g Mg, and about 22 mg/g Na. In another exemplary embodiment, traditional kappa carrageenan extract may contain about 49 mg/g K, about 20 mg/g Ca, about 0.4 mg/g Mg, and about 10 mg/g Na. In another exemplary embodiment, neutral kappa carrageenan extract may contain about 48 mg/g K, about 4 mg/g Ca, about 5 mg/g Mg, and about 11 mg/g Na.

In exemplary embodiments, the carrageenan extracts provided in the above traditional treated or neutral treated extraction process have a characteristic gelling temperature ($T_G$) and melting temperature ($T_M$). For example, a traditional iota carrageenan having the above gelling cation content may have a $T_G$ of about 40° C. and a $T_M$ of about 47° C. A neutral iota carrageenan having the above gelling cation content may have a $T_G$ of about 25° C. and a $T_M$ of about 38° C. A traditional kappa carrageenan having the above gelling cation content may have a $T_G$ of about 37° C. and a $T_M$ of about 62° C. A neutral kappa carrageenan having the above gelling cation content may have a $T_G$ of about 38° C. and a $T_M$ of about 52° C.

In various embodiments, the carrageenan extract may be provided in an extract solution. For example, a dried extract may be dissolved in water to form an extract solution, or where the extract is made under alkali conditions, the extract solution may be the solution that results from a neutralization step. In exemplary embodiments, an extract solution may include from about 1% to about 5% carrageenan, more preferably about 2% carrageenan (i.e., about 20 grams of carrageenan extract per 1000 grams of solution).

According to the exemplary embodiments, the carrageenan extract may be contacted with an ion exchange material. Ion exchange is a reversible chemical reaction in which an ion in a fluid medium (such as an aqueous solution) is exchanged for a similarly charged ion attached to an immobile solid particle that is insoluble in the fluid medium. The term "ion exchange material" or "ion exchange resin," as used herein, refers to all such substances. The ion exchange resin is rendered insoluble due to the crosslinked nature of the polymeric support to which the ion exchanging groups are attached. Ion exchange resins are classified as acidic cation exchangers, which have positively charged mobile ions available for exchange, and basic, anion exchangers, which have available negatively charged ions, typically hydroxide ions.

In various exemplary embodiments, the ion exchange material is an acidic cationic exchange resin. Exemplary acidic cationic exchange resins include organic acid exchange resins, such as a sulfonic acid cation exchange resin, a carboxylic acid cation exchange resin, an acrylic acid cation exchange resin or a phosphoric acid cation exchange resin. In various exemplary embodiments, the ion exchange material is a sulfonic acid cation exchange material. Exemplary sulfonic acid cation exchange resins include, for example, sulfonated styrene-divinylbenzene copolymers, sulfonated crosslinked styrene polymers, phenol-formaldehyde-sulfonic acid resins, benzene-formaldehyde-sulfonic acid resins, and combinations and mixtures thereof. In various exemplary embodiments, the ion exchange resin may be provided in its acid form, or in its metal ion form, i.e., sodium form. Acidic cation exchange resins such as those described above, are commercially available. An exemplary cation exchange resin includes a sodium ion form of a strong acid cation exchange resin based on a styrene-divinylbenzene copolymer, such as those sold under the following trade names: LEWATIT S 1468, by LANXESS AG; and AMBERLITE 252 Na, AMBERLITE 200C Na, and AMBERLITE IR120 Na, by the Rohm and Haas Company. Using the guidance provided herein, one familiar with the technology would be able to select a suitable acidic cation exchange resin for use with the exemplary embodiments.

In the exemplary embodiments, as a result of the ion-exchange process step, the carrageenan extract may have reduced levels of gelling cations. For example, in an exemplary embodiment in which the ion exchange material is a sodium form acidic cation exchange resin, when the carrageenan extract contacts the ion-exchange material the carrageenan's divalent ions Ca and Mg may be reduced, and exchanged for monovalent Na ions. For traditional iota carrageenan, the exemplary ion-exchange process step may reduce the Ca content to below about 13 mg/g, and may reduce the Mg content to below about 2 mg/g, and may increase the Na content to greater than about 45 mg/g. For neutral iota carrageenan, the ion-exchange process may reduce the Ca content to below about 5 mg/g, and may reduce the Mg content to below about 5 mg/g, and may increase the Na content to greater than about 45 mg/g. For traditional kappa carrageenan, the ion-exchange process step may reduce the Ca content to below about 7 mg/g, and may reduce the Mg content to below about 0.2 mg/g, and may increase the Na content to greater than about 30 mg/g. For neutral kappa carrageenan, the ion-exchange process may reduce the Ca content to below about 5 mg/g, and may reduce the Mg content to below about 5 mg/g, and may increase the Na content to greater than about 30 mg/g.

It also has been unexpectedly found that under certain process conditions, the ion-exchange process step also reduces the potassium levels in the carrageenan extract. For example, in traditional and neutral iota carrageenan, the K levels may be reduced to less than 35 mg/g; in traditional and neutral kappa carrageenan, the K levels may be reduced to less than 30 mg/g.

Without intending to be bound by any particular theory, it is believed that the reduction in the gelling cations, particularly the K, Ca, and Mg cations, corresponds to a reduction in the gelling and melting temperature of the carrageenan. For example, by decreasing the gelling cations, a traditional iota carrageenan may have a reduced $T_G$ between about 18° C. and 30° C., and a reduced $T_M$ between about 27° C. and about 37° C. For neutral iota carrageenan, reducing the gelling cations may result in a reduced $T_G$ between about 5° C. and about 17° C., and a reduced $T_M$ between about 17° C. and about 27° C. For traditional kappa carrageenan, reducing the gelling cations may result in a reduced $T_G$ between about 10° C. and about 27° C., and a reduced $T_M$ between about 23° C. and about 45° C. For neutral kappa carrageenan, reducing the gelling cations may result in a reduced $T_G$ between about 10° C. and about 35° C., and a reduced $T_M$ between about 23° C. and about 45° C.

According to the various exemplary embodiments, the amount of ion exchange material used will vary depending on the concentration of the carrageenan extract in the extract solution—for higher concentrations of extract in the extract solution, more ion exchange material will have to be used to obtain the same effect as with extract solutions of lower concentration. In exemplary embodiments, the concentration of the ion exchange material may range from about 0.5 g/g carrageenan to about 10 g/g carrageenan in the solution, more preferably about 1.25 g/g carrageenan to about 10 g/g carrageenan in solution, and more preferably from about 2.5 g/g carrageenan to about 10 g/g carrageenan in solution. In exemplary embodiments, in which the extract solution comprises 2% carrageenan extract, the concentration of the ion exchange material may range from about 10 g/l to about 200 g/l, more preferably about 25 g/l to about 200 g/l, and more preferably from about 50 g/l to about 200 g/l.

In accordance with the exemplary embodiments, the temperature during the ion exchange process step must be high enough to ensure that the carrageenan is dissolved, but low enough to prevent damage to the ion exchange resin. In various exemplary embodiments, the temperature of the ion exchange process step may be within the range of about 30° C. to about 90° C., preferably from about 50° C. to about 80° C., and more preferably from about 60° C. to about 70° C.

In the various exemplary embodiments, the ion exchange process step takes place very fast, and the ion exchange step is suited for a continuous process. For example, the carrageenan extract or solution may be passed through a column packed with ion exchange resin, in which the flow rate of the extract and the height of the column determine, in part, the extent to which the extract may be ion exchanged. In embodiments in which the ion exchange process may be conducted in a batch process, the ion exchange process step may take about 5-30 minutes, preferably 20-30 minutes.

In various exemplary embodiments, the ion-exchanged carrageenan may be precipitated, dried and/or ground according to known techniques. In an exemplary embodiment, the ion-exchanged powdered carrageenan extract may be used by itself in a composition or consumer product. Other aspects of the processes for production of carrageenan according to the exemplary embodiments are not particularly limited, and where necessary, conventional carrageenan technology may be used. In addition to the specific steps set forth herein, processes of the exemplary embodiments may further comprise additional processes typically associated with carrageenan production.

In various exemplary embodiments, the ion-exchanged carrageenan may be combined or mixed or blended with one or more additional carrageenan extracts. In these embodiments, it is envisioned that like carrageenan types will be used together, i.e., iota carrageenan will be combined with iota carrageenan, and kappa carrageenan will be combined with kappa carrageenan. It has been unexpectedly found that blending the ion-exchanged carrageenan, with an additional carrageenan extract provides a composition having unique gelling and melting characteristics. Without intending to be bound by a particular theory, it is believed that when mixed the two carrageenan materials interact and share ions, resulting in a carrageenan composition having hybrid properties, rather than merely a mixture of two different carrageenans. For example, if an ion-exchanged carrageenan having a first $T_G$ and first $T_M$ is mixed with a non-ion-exchanged carrageenan having a second $T_G$ and second $T_M$ that are higher than the first $T_G$ and first $T_M$, respectively, the resultant carrageenan mixture would have a third $T_G$ that is between the first and second $T_G$ and third $T_M$ that is between the first and second $T_M$. The resultant $T_G$ and $T_M$ of the carrageenan mixture is related to the ratio of the amounts of the two initial carrageenan fractions. Similarly, the carrageenan mixture also may have a gelling cation content that is between the content of the two initial carrageenan fractions, related to the proportion of the two initial carrageenan fractions. (This is further illustrated in the Examples, below). By controlling the proportion of the two initial carrageenan fractions, one may control the properties of the carrageenan mixture.

In various embodiments, the ion-exchanged carrageenans may be combined with non-ion-exchanged or ion-exchanged carrageenan compositions such as those disclosed in previous applications discussed in the above filed U.S. Patent Applications and also in U.S. Patent Application Publication No. 2008-0317926, U.S. Patent Application Publication No. 2008-0317790, U.S. Patent Application Publication No. 2008-0317789, and U.S. Patent Application Publication No. 2008-0317791, the disclosures of which are incorporated herein by reference in their entirety.

In exemplary embodiments, the two or more carrageenans may be combined in solution or gel form. In other exemplary embodiment, the two or more carrageenans may be processed individually to dry powders, and then mixed together in the dry form. During preparation of gels, the cations present in the two or more fractions may interchange to form a carrageenan mixture as described above.

Figure 13:
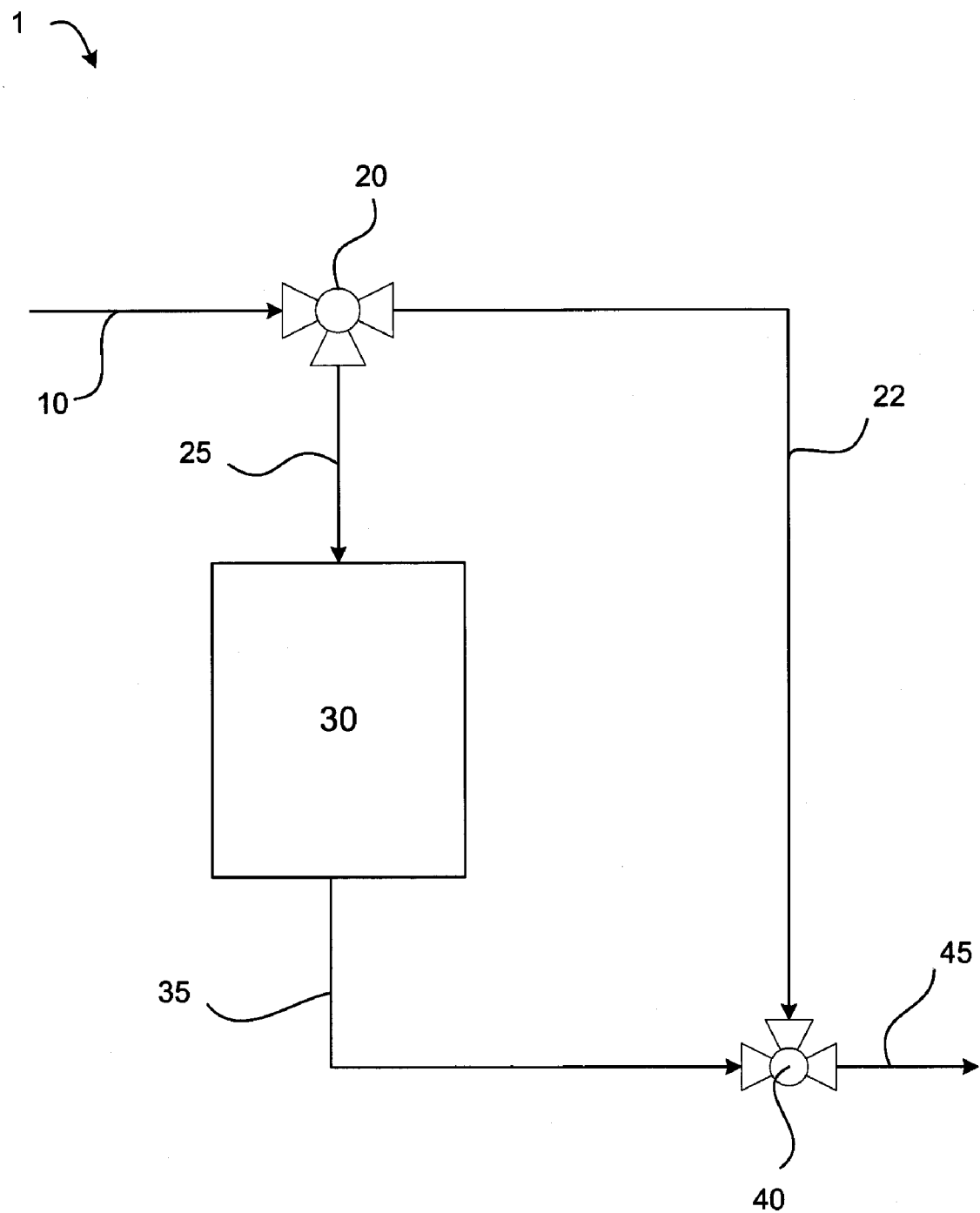
FIG. 13 shows an exemplary process for making an ion exchanged carrageenan mixture in accordance with the exemplary embodiments.

Various exemplary embodiments provide a process for making a mixture including the ion-exchanged carrageenan extract. Referring to FIG. 13, in an exemplary process 1, a carrageenan extract 10 (such as a traditionally or neutrally extracted iota or kappa carrageenan extract) may pass under pressure to a valve 20. Valve 20 may be any device capable of controllably splitting the flow from input passage 10 into two portions: a first extract portion 22, and a second extract portion 25. For example, valve 20 may be a distribution valve or other like device. The value 20 may direct the second extract portion 25 to and into an ion exchanger 30. In exemplary embodiments, the ion exchanger 30 houses an ion-exchange material, such as a sodium form acidic cation exchanger. The amount of the ion-exchange material, and the rate of fluid flow through the ion exchanger may determine the efficiency of the ion exchange process (i.e., the amount of ions exchanged). As the second extract portion 25 flows through the ion exchanger 30, the carrageenan of the second extract portion contacts the ion-exchange material, reducing the gelling cation content of the carrageenan to produce an ion-exchanged second extract portion 35. The ion-exchanged second extract portion 35 and the first extract portion 22 meet at a connector 40. Connector 40 may be any device capable of combining the ion exchanged second extract portion 35 and the first extract portion 22 to produce a carrageenan mixture 45. For example, connector 40 may be a blend valve or a T-Connector. Using the guidance provided herein, one familiar with fluid flow systems would understand how to select devices suitable for valve 20, ion exchanger 30, and connector 40, as well as other elements of process 1.

In accordance with the exemplary embodiments, a means may be provided to control the flow through the process 1, either automatically or manually. For example, a means may be provided for adjusting the flow into and/or out of valve 20, and/or connector 40. One or more sensors (e.g., fluid flow sensors, temperature sensors, pressure sensors, etc.) may be disposed on one or more passageways and valves to monitor the fluid flow through the process 1. These sensors may generate signals that may be transmitted to an input/output device such as a computer or other display terminal. A human operator may monitor these signals and adjust the flow through valve 20 and/or connector 40, or other process settings. Alternatively, the adjustment of the process setting may be automated, such as with a pre-programmed algorithm in a computer program. Using the guidance provided herein, one familiar with fluid flow systems would understand how to select a suitable means for controlling the fluid flow through the process 1.

In accordance with the exemplary embodiments, the process 1 may be used to produce a carrageenan extract having a pre-determined gelling and melting temperature. A non-ion exchanged carrageenan extract (i.e., such as a traditionally or neutrally extracted iota or kappa carrageenan extract) having a first $T_G$ and $T_M$ may be dissolved in water to produce a extract solution 10 that may be pumped under pressure to valve 20. Valve 20 may then split the extract solution 10 into two portions: a first portion 22, having first $T_G$ and $T_M$ same as the extract solution; and a second portion 25, which is directed to the ion exchanger 30, which converts the second portion 25 to an ion-exchanged second portion 35 having a second $T_G$ and $T_M$ that is lower than the first $T_G$ and $T_M$. When the first portion 22 and the ion-exchanged second portion 35 are combined at connector 40, the resultant carrageenan mixture 45 has a third $T_G$ and $T_M$, that is between the first and second $T_G$ and $T_M$, respectively. The valve 20 and/or the connector 40 may be adjusted to change the ratio of the amount of the first portion 22 to the amount of the ion-exchanged second portion 35 that are combined to produce the carrageenan mixture 45. The third $T_G$ and $T_M$ will vary in proportion to the ratio of the first portion 22 to the ion exchanged second portion 35. In other words, the melting and gelling temperatures may be increased or decreased by controlling the settings of valve 20 and/or connector 40 to regulate the proportion of the first portion 22 to the ion-exchanged second portion 35.

In various exemplary embodiments, the ion-exchanged carrageenan or a mixture including the ion-exchanged carrageenan may be used in various products. The ion-exchanged carrageenan is particularly beneficial in products in which gelling and/or melting must take place at lower temperatures than what is possible with conventional carrageenan products. For example, the carrageenan products of the exemplary embodiments may be incorporated into various products such as air freshener gels; water-in-oil emulsions (such as skin care lotions and low-fat margarines); pharmaceuticals such as capsules; and processed meat, poultry and fish products. These products are discussed in greater detail below and in U.S. Patent Application Publication No. 2008-0317683, the disclosure of which is incorporated herein by reference in its entirety.

In exemplary embodiments, the ion-exchanged carrageenan or a mixture including the ion-exchanged carrageenan may be used in household products such as air freshener gels. Exemplary air freshener gels contain one or more non-ionic surfactants, and when the gels are heated above a certain point (referred to as the "cloud point", typically non-ionic surfactants have a cloud point in the range of about 0° C. to about 60° C.) the non-ionic surfactants become less soluble and precipitate out of the gel leading to a cloudy, non-transparent gel. The carrageenan products of the present invention can be tailored to gel at or below the cloud point of the surfactant, thus, preventing the surfactant crystals from being frozen in the gel and so preventing the resulting air freshener gel from becoming cloudy, and non-transparent.

In exemplary embodiments, the ion-exchanged carrageenan or a mixture including the ion-exchanged carrageenan may be used in a cold setting air freshener gel. Conventional air freshener gels are made by heating the composition to about 70-90° C., after which gelation takes place during cooling. However, the heating provides for a substantial loss of the fragrance used in the air freshener formulation as some of the fragrance material evaporates during heating. Carrageenan products of the exemplary embodiments can be tailored to dissolve at temperatures at or below room temperature, which eliminates the loss of fragrances. Once dissolved, the liquid air freshener formulation can be poured into its final container, which contains gelling cations (as discussed above) that in conjunction with the carrageenan form the gel network. Such cations may be added directly into the container before filling the air freshener formulation into the container, or the cations may be added as a coating, such as a film coating, with which the container is pre-coated. As the cations diffuse into the air freshener formulation under quiescent conditions, the air freshener formulation will gel into a homogeneous gel.

In exemplary embodiments, the ion-exchanged carrageenan or a mixture including the ion-exchanged carrageenan may be used in water-in-oil emulsions, such as those for use in food products or personal care products. Water-in-oil emulsions are characterized by a continuous oil phase in which a discontinuous phase of water droplets are dispersed. In many cases it is desired that the water-in-oil emulsion inverts into an oil-in-water emulsion at a specific temperature so that the emulsion releases its water soluble constituents. An example is margarine, where the emulsion inverts in the mouth to release water soluble aromas and salts. Gelatine is the preferred stabilizer of the water phase, since gelatine ensures that the aqueous phase melts at the same temperature as the oil phase. That temperature is about the temperature in the mouth, and thus, through the saliva and the shear in the mouth, the emulsion inverts to an oil-in-water emulsion and releases aroma and salt. Conventional carrageenan products are unable to form gels that melt at the temperature in the mouth, but carrageenan products of the present invention can be tailored to do just that.

With respect to personal care products, most skin care lotions are produced as oil-in-water emulsions, in which the water phase is the continuous phase. This is disadvantageous because it requires the use of preservatives in skin care lotion formulations. There is a desire to eliminate preservatives in skin care lotions, particularly preservatives of the paraben type, because they have some similarity with hormones. Use of carrageenan products of the exemplary embodiments makes it possible to provide a skin care lotion in the form of an water-in-oil emulsion. In these water-in-oil emulsions, the oil continuous phase does not require preservatives, but the water-in-oil emulsion will invert to a spreadable oil-in-water emulsion at the temperature of the skin and the shear from rubbing in the lotion. In one exemplary embodiment, the ion-exchanged carrageenan or a mixture including the ion-exchanged carrageenan may be used in a water-in-oil emulsion comprising 20-80% oil, and the emulsion inverts at a temperature in the range of about 37-50° C.

In various exemplary embodiments, the ion-exchanged carrageenan or a mixture including the ion-exchanged carrageenan may be used for encapsulation, such as for flavour encapsulation or encapsulation of drugs. In cases where the agent being encapsulated is heat sensitive, the ion-exchanged carrageenan products of the exemplary embodiments can encapsulate the agent at low temperatures. The ion-exchanged carrageenan or carrageenan mixture may also be specially formulated to release the encapsulated agent within a predetermined target temperature range, by changing the ion-exchange properties, or by blending two carrageenans at a ratio calculated to provide the a carrageenan having the desired $T_G$ and $T_M$. In one exemplary embodiment, the ion-exchanged carrageenan or a mixture including the ion-exchanged carrageenan may be used in a pharmaceutical product to encapsulate a drug that must be released at temperatures in the range of about 37-50° C.

In various exemplary embodiments, the ion-exchanged carrageenan or a mixture including the ion-exchanged carrageenan may be used in processed meat, poultry and fish products. Processed meat, poultry and fish products are often heat treated at pasteurization temperature, which is about 72° C. The aqueous phase of such products typically contain up to about 3% sodium chloride, which precludes the dissolution of conventional carrageenan products. Carrageenan products of the present invention can be tailored to dissolve at a temperature at or below the pasteurization temperature, which leads to dissolution of the carrageenan product and thus, a more homogeneous gel in the final processed meat, poultry or fish product.

The exemplary embodiments will now be explained in greater details with respect to the following non-limiting examples. These examples and their accompanying textual descriptions, will present detailed descriptions of the process of the exemplary embodiments as well as results obtained from the experimental process. Additionally analysis of the results will be presented and supplemented by possible theoretical explanations.

Experimental Methods

The following experimental equipment, materials and methods were used in carrying out the present experiments. Application of these experimental methods are introduced in the specific examples section below that illustrate the exemplary embodiments and place it within the context of the prior art.

Equipment

Magnetic stirrer and heater equipped with temperature control, e.g., Ikamag Ret produced by Janke & Kunkel GmbH, Germany.

Beakers, 1 litre and 2 liters.

2 liters conical flask, Büchner funnel and vacuum pump.

Filter cloth.

Rheometer—Haake RheoStress RS 100 equipped with cup Z20/48 mm and rotor Z20 DIN produced by Thermo Electron GmbH, Germany.

Analytical balance, weighing with two decimals—Sartorius Basic B3100P produced by Sartorius GmbH, Germany.

Autoclave, 25 liters

Chemicals:

Sodium methyl-4-hydroxybenzoate, analytical, Merck, KGaA, Darmstadt, GermanyIsopropyl alcohol, 100%

Glycerine, analytical, Scharlau Chemie, Barcelona, Spain

Lemon oil, H.N. Fusgaard, Roedovre, Denmark

Cremophor RH 40, BASF, Ludwigshafen, Germany

Ion exchange resin, Lewatit® S-1468, sodium form acidic cationic exchange resin, LANXESS, Leverkusen, Germany Traditional Carrageen Extraction Method:

"Traditional" Carrageenan Extraction was carried out according to U.S. Pat. No. 3,094,517 and U.S. Pat. No. 3,907,770, as described above, and specifically according to the following steps:

1. Carrageenan was extracted with a surplus of calcium hydroxide and left at high temperature for 24 hours to provide complete alkali modification.
2. The extract was then filtered, neutralized to pH about 9 with carbon dioxide, filtered again and precipitated in three volumes of 100% isopropanol.
3. The precipitate was then pressed by and dried at 70° C. over night and then milled on a 0.250 mm sieve.

Neutral Carrageen Extraction Method:

Neutral Extraction of seaweed with demineralized water was carried out according to the following process:

1. Seaweed was washed three times in 1 liter demineralized water and kept in a refrigerator.
2. About 130 g washed seaweed was placed in a 10-liter beaker.
3. 7500 ml boiling demineralized water was added and extraction performed at 90° C. for 1 hour.
4. The extracted seaweed was filtered using diatomaceous earth as filter aid.
5. The filtered extract was precipitated in three volumes 100% isopropanol, pressed by hand and dried at 70° C. over night; then finally milled on a 0.250 mm sieve.

Ion Exchange of Dissolved Carrageenan:

1. 20 g. dry carrageenan was dispersed in 1 liter demineralized water and dissolved by heating to 70° C. while stirring (producing a 2% solution).
2. Various amounts of ion exchange resin were added to the hot solution, and the mix was allowed to stand at 70° C. for various periods of time.
3. Afterwards, the mix was filtered on a nylon cloth, and the liquid was precipitated in three volumes of 100% isopropyl alcohol, and washed once in 500 ml 100% isopropyl alcohol.
4. The precipitate was dried at 70° C. over night and milled on 0.250 mm sieve.

Ion Exchange of Neutral Kappa Carrageenan Seaweed Extract:

Ion Exchange of neutral kappa carrageenan extract was conducted as follows:

1. 600 g dry *E. cottonii* seaweed was washed four times in water from the production plant.
2. The washed seaweed was placed in an autoclave with 15 liters water from the production plant and extracted at 100° C. for 30 minutes.
3. The extracted seaweed was sieved and allowed to stand for 3-4 hours at a temperature of about 90° C.
4. The extract was filtered on a diatomaceous filter, and a small sample was precipitated in isopropyl alcohol to determine the concentration of carrageenan.
5. Samples of the extract were ion exchanged with different amounts of ion exchange resin at 70° C. for 30 minutes.
6. The ion exchange resin was removed with a sieve and the extracts were precipitated in 3 volumes isopropyl alcohol.

Determination of Gelling and Melting Temperatures for Carrageenan

The determination of gelling and melting temperatures of carrageenan-compositions was made using a composition with the following carrageenan-incorporating composition:

| Ingredients | Grams | % |
| --- | --- | --- |
| Seaweed extract | 0.48 | 0.96 |
| Glycerin | 3.00 | 6.00 |
| Parabene | 0.05 | 0.10 |
| Demineralized Water | 33.75 | 67.50 |
| Lemon oil | 1.25 | 2.50 |
| Isopropyl alcohol | 1.50 | 3.00 |
| Cremophor RH 40 | 10.00 | 20.00 |
| Net weight | 50.00 | 100.00 |

This composition was prepared as follows:

1. The water, glycerine and parabene were mixed.
2. The seaweed extract was dispersed in this mixture and stirred for about 60 minutes.
3. The dispersion was heated while stirring to 70° C.
4. The dispersion was then cooled to 55-60° C.
5. A hot (about 50° C.) preparation of lemon oil, isopropyl alcohol and Cremophor RH 40 was mixed into the cooled dispersion.
6. The net weight was adjusted with hot (about 60° C.) water and cooled over night at room temperature.

The gelling and melting temperatures were measured by temperature sweeps on Haake RheoStress RS100, using cooling and heating rates of 1° C./min. The following program was generally used, however, in some instances where gelling and melting temperatures were higher; the program was run at higher starting temperatures and lower end-temperatures:

1. 65-5° C., 0.50 Pa, f=0.4640 Hz
2. 5-65° C., 0.50 Pa, f=0.4640 Hz
3. Gelling temperature is defined as the temperature during the cooling sweep, where the elastic modulus, G' intersects with the viscous modulus, G".
4. Melting temperature is defined as the temperature during the heating sweep, where the elastic modulus, G' intersects with the viscous modulus, G".

EXAMPLES

The invention will now be described in more detail with respect to the following non-limiting examples which were performed with the above described equipment, materials and methods.

The following Example relates to results obtained by treating *Eucheuma cottonii* and *Eucheuma Spinosum* by the "traditional" method and "neutral" extraction methods. Additional carrageenan material was prepared according to the exemplary embodiments by subjecting it to the ion-exchange process. Thus the results obtained from the carrageenan treated in an ion-exchange process were compared with comparative, prior art "traditional" and "neutral" extractions.

Example 1

Ion Exchange of Traditional and Neutral Kappa Carrageenan

In this example *Eucheuma cottonii* was extracted, using the respective methods provided above, to produce "Traditional Kappa Carrageenan" and "Neutral Kappa Carrageenan." Solutions (2% carrageenan solutions) of these extracts were then ion exchanged, using the method provided above, with the sodium form acidic cationic ion exchange resin in concentrations of 50 g/l, 100 g/l, and 200 g/l (2.5 g/g carrageenan, 5 g/g carrageenan, and 10 g/g carrageenan, respectively). Each of the sample solutions was precipitated in three volumes 100% isopropyl alcohol, dried over night at 70° C. and milled on 0.250 mm sieve. Gelling ion content, gelling temperature ($T_G$) and melting temperature ($T_M$) were measured for each non-ion-exchanged control sample (identified as 0 g/l) and ion-exchanged sample. The results are set forth in Tables 1 and 2, below, as well as in FIGS. 1-3.

TABLE 1

Effect of Ion Exchange on Cation Content
and $T_G$ and $T_M$ of "Traditional Kappa Carrageenan"

| Ion Exchange Material g/l of 2% solution | Time Min | $T_G$ ° C. | $T_M$ ° C. | Na mg/g | K mg/g | Ca mg/g | Mg mg/g |
|---|---|---|---|---|---|---|---|
| 0 | 0 | 37 | 62 | 9.50 | 49.40 | 20.20 | 0.36 |
| 50 | 30 | 19 | 26 | 49.30 | 17.80 | 0.22 | 0.10 |
| 100 | 30 | 17 | 24 | 53.80 | 9.20 | 0.13 | 0.10 |
| 200 | 30 | 11 | 23 | 55.70 | 4.90 | 0.09 | 0.09 |
| 1:1 Mixture of 0 and 100 | 5 | 28 | 47 | 28.50 | 29.20 | 9.10 | 0.21 |
| 1:1 (0, 100) | 15 | 28 | 48 | 29.00 | 29.80 | 9.20 | 0.22 |
| 1:1 (0, 100) | 30 | 28 | 47 | 29.20 | 29.50 | 9.20 | 0.21 |
| 1:1 (0, 100) | 60 | 28 | 48 | 29.00 | 29.50 | 9.10 | 0.21 |
| 1:1 (0, 100) | 1020 | 28 | 48 | 28.90 | 29.50 | 9.20 | 0.21 |

TABLE 2

Effect of Ion Exchange on Cation Content
and $T_G$ and $T_M$ of "Neutral Kappa Carrageenan"

| Ion Exchange Material g/l of 2% solution | Time Min | $T_G$ ° C. | $T_M$ ° C. | Na mg/g | K mg/g | Ca mg/g | Mg mg/g |
|---|---|---|---|---|---|---|---|
| 0 | 0 | 38 | 52 | 11.40 | 48.00 | 3.90 | 5.10 |
| 50 | 30 | 29 | 35 | 45.20 | 11.80 | 0.11 | 0.09 |
| 100 | 30 | 13 | 27 | 49.10 | 6.70 | 0.10 | 0.05 |
| 200 | 30 | 10 | 23 | 50.30 | 3.60 | 0.09 | 0.05 |
| 1:1 Mixture of 0 and 100 | 5 | 26 | 42 | 29.00 | 28.10 | 2.10 | 2.56 |
| 1:1 (0, 100) | 15 | 27 | 43 | 29.00 | 28.40 | 2.10 | 2.58 |
| 1:1 (0, 100) | 30 | 26 | 43 | 29.00 | 28.00 | 2.00 | 2.56 |
| 1:1 (0, 100) | 60 | 26 | 42 | 29.20 | 28.20 | 2.00 | 2.54 |
| 1:1 (0, 100) | 1055 | 26 | 42 | 30.10 | 29.00 | 2.10 | 2.59 |

As can be seen in the above tables and in FIG. 1, by contacting the kappa carrageenan samples with the sodium form acidic cationic ion exchange material, gels made with traditional and neutral kappa carrageenan had reduced $T_G$ and $T_M$. In addition, the $T_G$ and $T_M$ decreased as the ion-exchange concentration increased, eventually tapering off as the concentration approached 200 g/l. For traditional kappa carrageenan samples, the $T_G$ for the ion-exchanged samples ranged from about 10° C. to about 27° C., and the $T_M$ ranged from about 23° C. to about 45° C. For the neutrally extracted kappa carrageenan samples, the $T_G$ for the ion-exchanged samples ranged from about 10° C. to about 35° C., and the $T_M$ ranged from about 23° C. to about 45° C.

Figure 2:
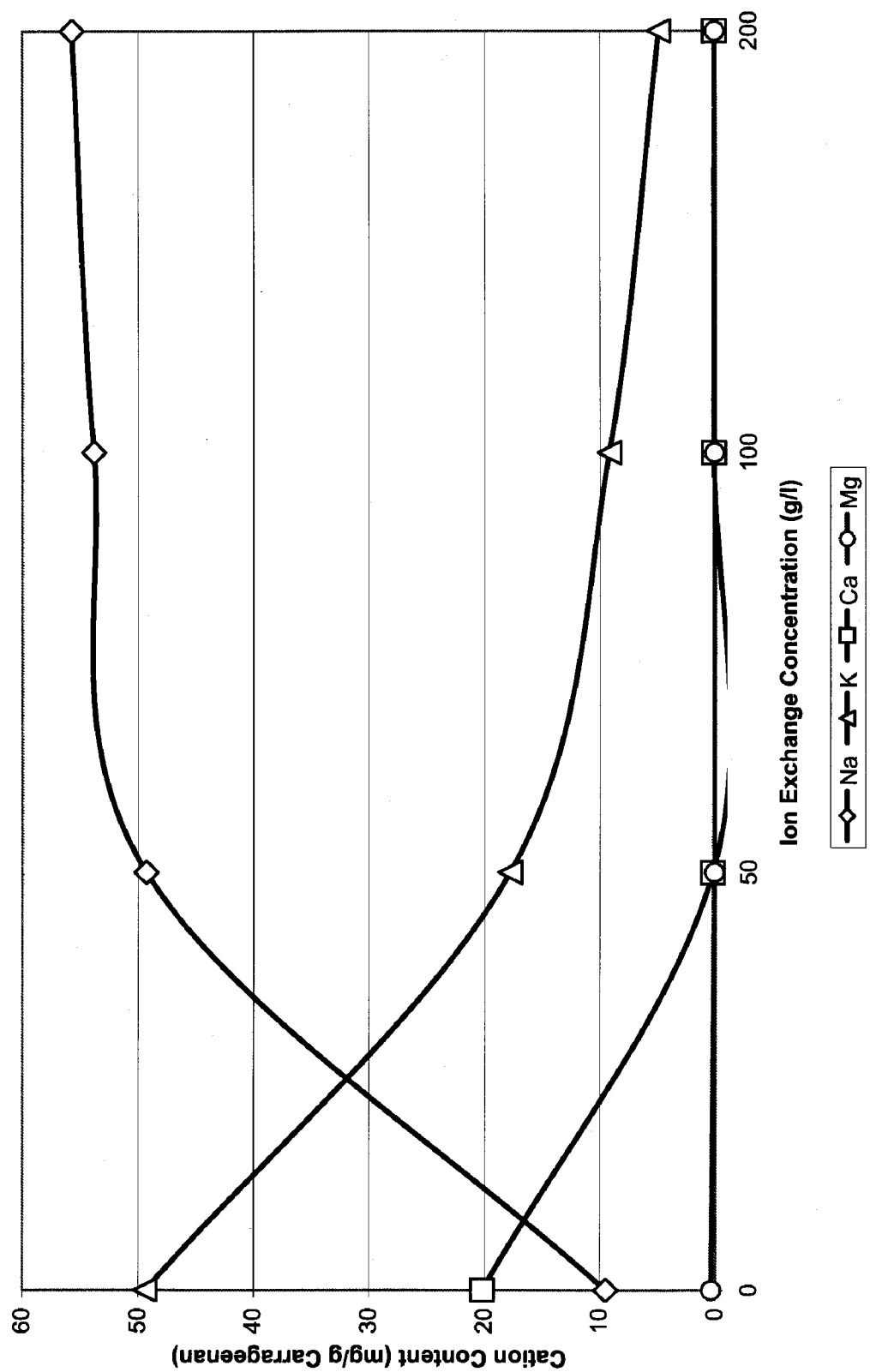
FIG. 2 shows the effect of ion exchange material concentration on cation composition of traditional kappa carrageenan.
Figure 3:
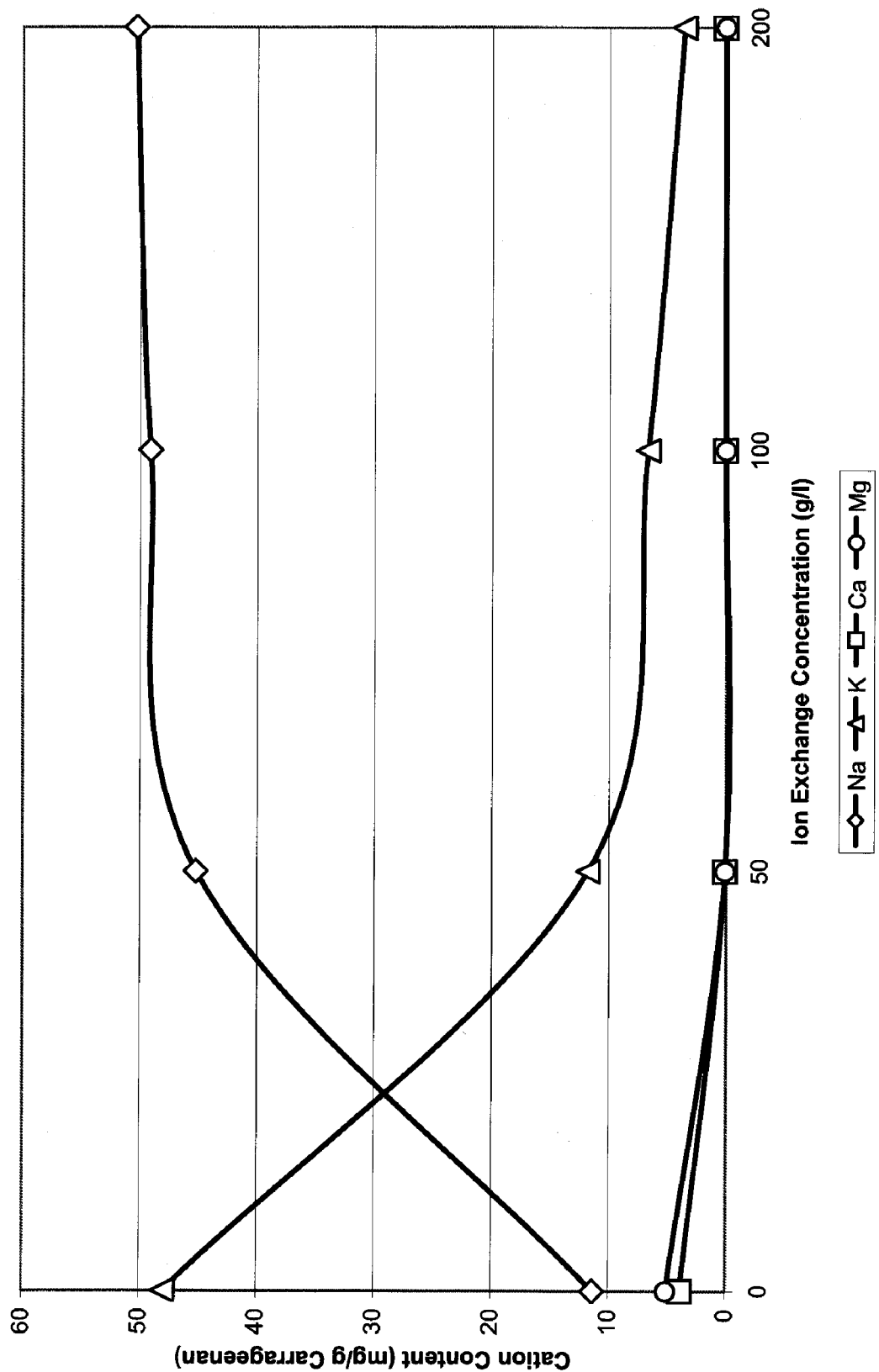
FIG. 3 shows the effect of ion exchange material concentration on the cation composition of neutral kappa carrageenan.

As can be seen in the above tables and in FIGS. 2 and 3, by contacting the kappa carrageenan samples with the sodium form acidic cationic ion exchange material, the gelling cation content of the carrageenan was reduced. With the exception of the sodium ions, the levels of each of the cations decreased as the concentration of the ion exchange material increased. In contrast, the sodium levels increased with ion-exchange, as expected for a sodium form ion exchange resin. For the traditional kappa carrageenan samples, the Potassium content of the ion-exchanged samples ranged between 5 and 30 mg/g, the Calcium content of the ion-exchanged samples ranged between 0 and 7 mg/g, and the Magnesium content of the ion-exchanged samples ranged between 0 and 0.2 mg/g. For the neutral kappa carrageenan samples, the Potassium content of the ion-exchanged samples ranged between 4 and 30 mg/g, the Calcium content of the ion-exchanged samples ranged between 0 and 3 mg/g, and the Magnesium content of the ion-exchanged samples ranged between 0 and 3 mg/g. For all samples, the cation content eventually leveled off at about a 70 g/l concentration (based on interpolation of the data). In other words, for traditionally or neutrally extracted kappa carrageenan, the lowest level of gelling cations could be achieved with an ion exchange concentration of 70 g/l (3.5 g/g carrageenan) or higher.

Comparing the traditional kappa carrageenan data in Table 1 and FIGS. 1 and 2, of all of the gelling cations, potassium content was the most strongly correlated to the magnitude of the gelling and melting temperatures, particularly when the ion exchange concentration is higher than about 50 g/l (2.5 g/g carrageenan). Likewise, when comparing the neutral kappa carrageenan data in Table 2 and FIGS. 1 and 3, potassium content was the most strongly correlated to the magnitude of the gelling and melting temperatures, particularly when the ion exchange concentration is higher than about 50 g/l (2.5 g/g carrageenan).

Example 2

Mixtures of Kappa Carrageenans

Mixtures were prepared for both traditional and neutral kappa carrageenans as follow. A carrageenan mixture was prepared by mixing a non-ion-exchanged kappa carrageenan (indicated as 0 g/l) in a 1:1 ratio with a kappa carrageenan that was ion exchanged with 100 g/l sodium form acidic cationic ion exchange resin (5 g/g carrageenan). The mixtures were made at 70° C., and allowed to stand at 70° C. while stirring from 5 minutes to about 1000 minutes, with samples taken periodically during the mixing process. Each of the sample solutions was precipitated in three volumes 100% isopropyl alcohol, dried over night at 70° C. and milled on 0.250 mm sieve. Gelling ion content, $T_G$, and $T_M$ were measured for each mixture sample. The results are set forth in Tables 1 and 2, above, as well as in FIGS. 4-6.

Figure 4:
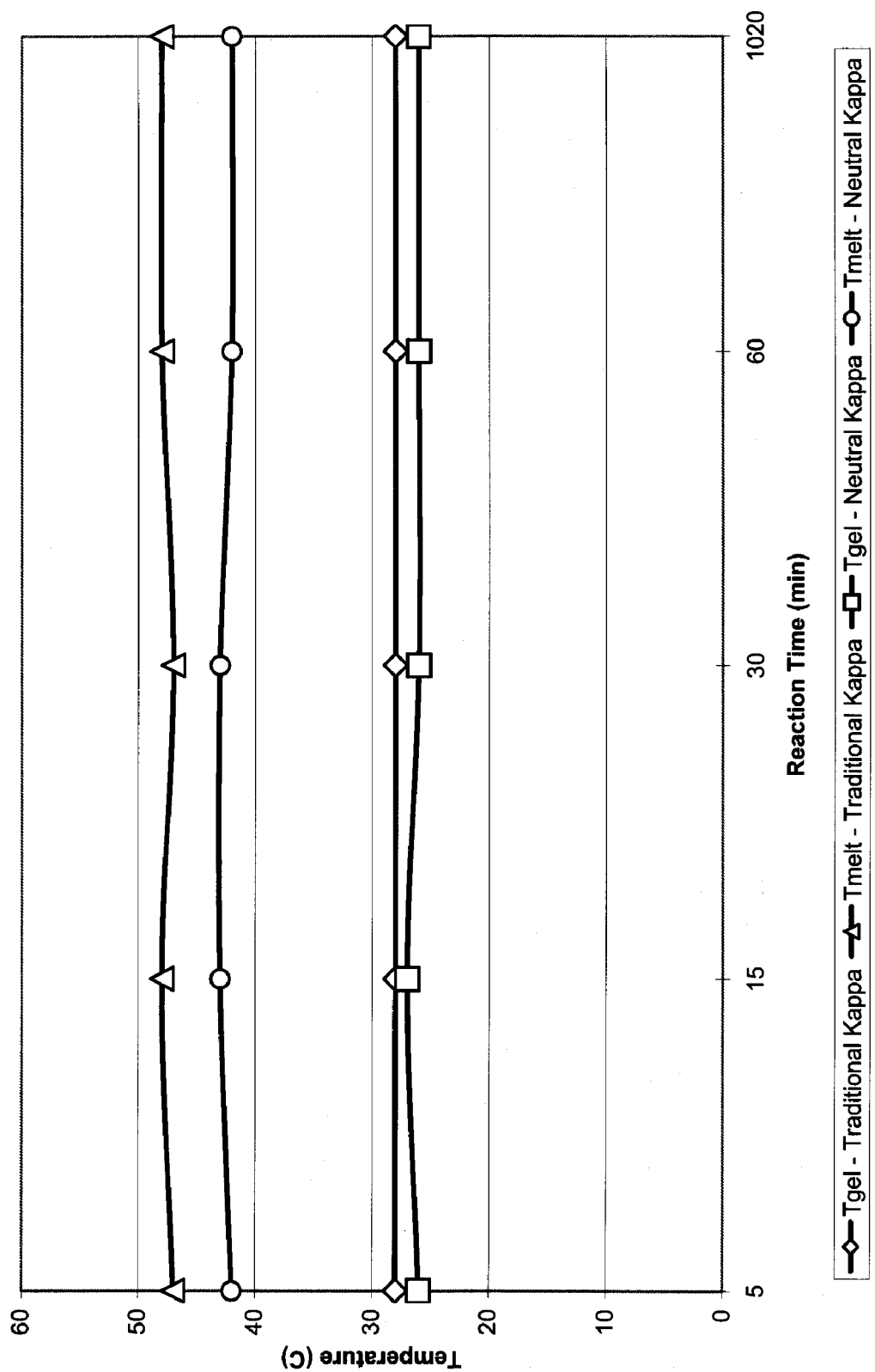
FIG. 4 shows the gelling and melting temperatures of a 1:1 mixture of a non-ion exchanged kappa carrageenan extract and a kappa carrageenan extract having been ion exchanged using 100 g ion exchange material per liter extract.
Figure 5:
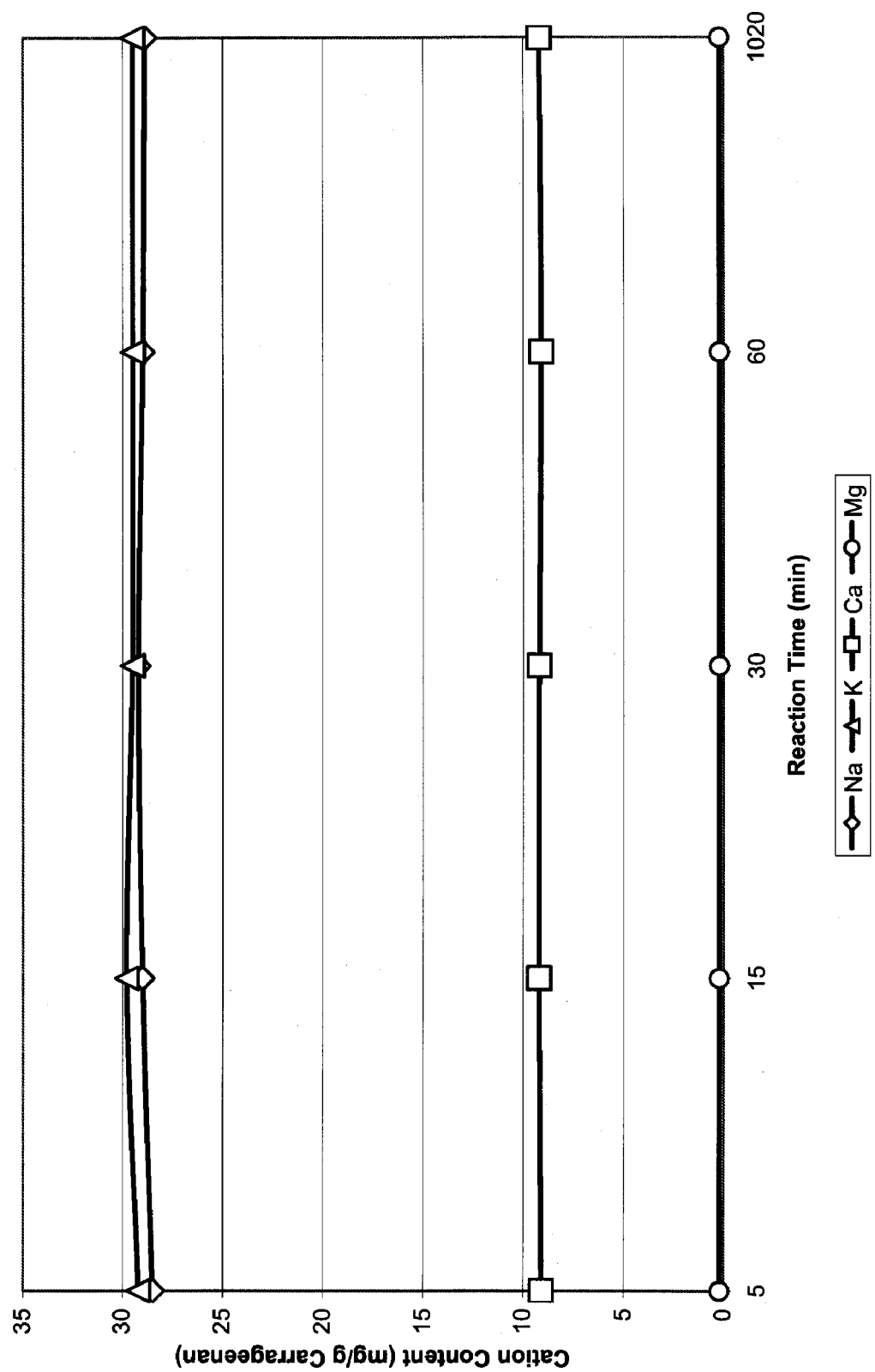
FIG. 5 shows the cation composition of a 1:1 mixture of traditional non-ion exchanged kappa carrageenan and traditional ion exchanged kappa carrageenan.
Figure 6:
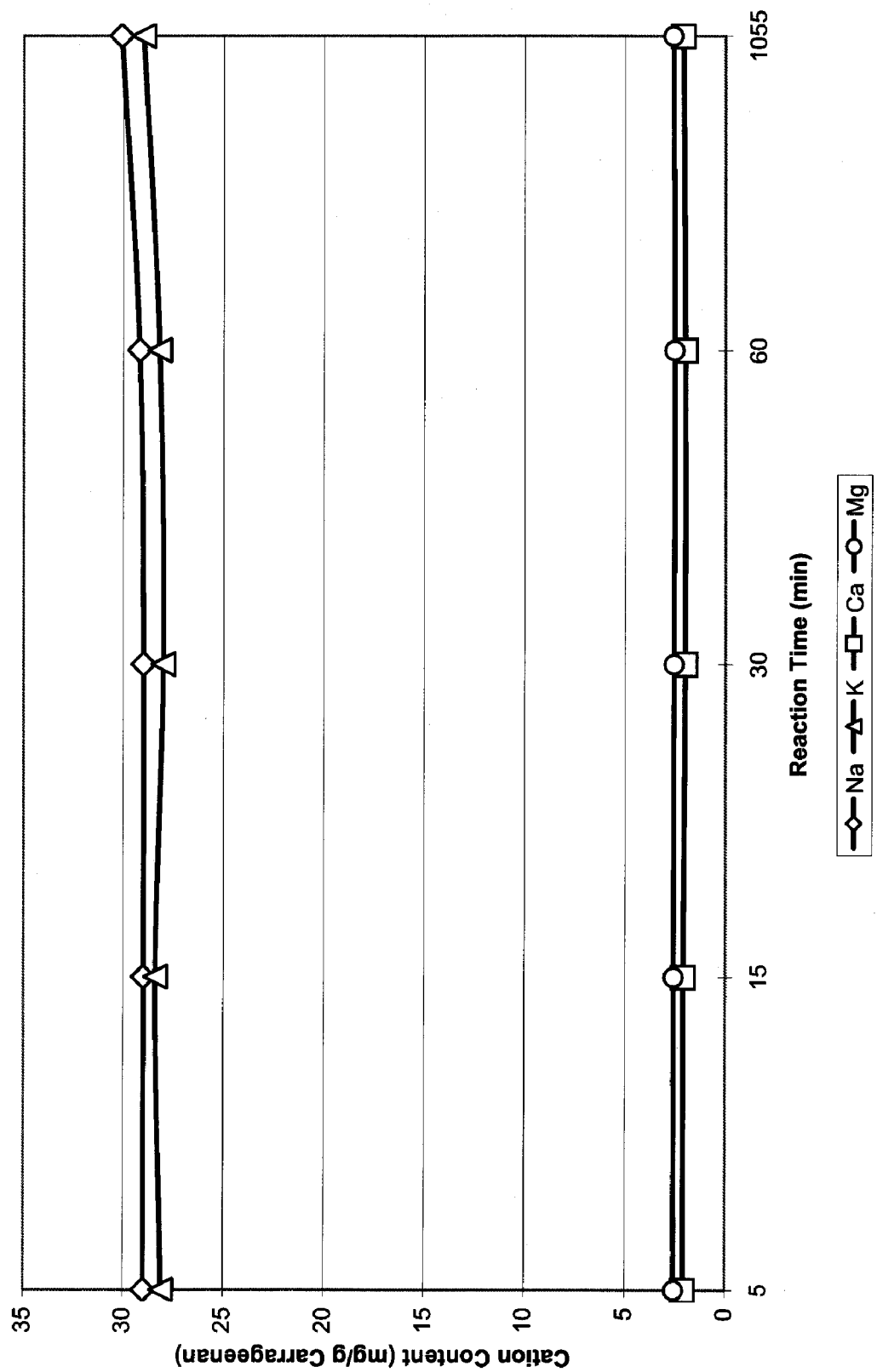
FIG. 6 shows the cation composition of a 1:1 mixture of neutral extracted non-ion exchanged kappa carrageenan and neutral extracted ion exchanged kappa carrageenan.

FIGS. 4-6 show the results of mixing a non-ion-exchanged kappa carrageenan with an ion-exchanged kappa carrageenan. FIG. 4 shows the $T_G$ and $T_M$ over time for a 1:1 mixture of non-ion-exchanged kappa carrageenan extract with kappa carrageenan extract that was ion exchanged at an ion exchange resin concentration of 100 g/l ion exchange resin (both traditional and neutral kappa carrageenans). As can be seen in FIG. 4 within 15 minutes of mixing the two carrageenan fractions, the $T_G$ and $T_M$ of the mixture was approximately the mid-point of the $T_G$ and $T_M$ of the respective individual kappa carrageenan fractions.

FIG. 5 shows the gelling cation composition over time for a 1:1 mixture of non-ion-exchanged traditional kappa carrageenan extract with traditional kappa carrageenan extract that was ion exchanged at an ion exchange resin concentration of 100 g/l. FIG. 6 shows the gelling cation composition over time for a 1:1 mixture of non-ion-exchanged neutral kappa carrageenan extract with neutral kappa carrageenan extract that was ion exchanged at an ion exchange resin concentration of 100 g/l. Here, the data shows that almost immediately upon mixing the two carrageenan fractions, the cation composition of the resulting mixture was approximately the mid-point of the cation composition of the respective individual kappa carrageenan fractions.

Example 3

Ion Exchange of Traditional and Neutral Iota Carrageenan

In this example, Eucheuma spinosum was extracted, using the respective methods provided above, to produce "Traditional Iota Carrageenan" and "Neutral Iota Carrageenan." Solutions (2% carrageenan solutions) of these extracts were then ion exchanged, using the method provided above, with sodium form acidic cationic ion exchange resin concentrations of 50 g/l, 100 g/l, and 200 g/l (2.5 g/g carrageenan, 5 g/g carrageenan, and 10 g/g carrageenan, respectively). Each of the sample solutions was precipitated in three volumes 100% isopropyl alcohol, dried overnight at 70° C. and milled on 0.250 mm sieve. Gelling ion content, $T_G$, and $T_M$ were measured for each non-ion-exchanged control sample (identified as 0 g/l) and ion-exchanged sample. The results are set forth in Tables 3 and 4, below, as well as in FIGS. 7-9.

TABLE 3

Effect of Ion Exchange on Cation Content and
$T_G$ and $T_M$ of "Traditional Iota Carrageenan"

| Ion Exchange Material g/l of 2% solution | Time Min | $T_G$ °C. | $T_M$ °C. | Na mg/g | K mg/g | Ca mg/g | Mg mg/g |
|---|---|---|---|---|---|---|---|
| 0 | 0 | 40 | 47 | 24.90 | 49.60 | 21.00 | 2.90 |
| 50 | 30 | 22 | 29 | 65.00 | 19.40 | 3.00 | 0.21 |
| 100 | 30 | 21 | 29 | 69.30 | 12.10 | 1.80 | 0.13 |
| 200 | 30 | 18 | 27 | 71.60 | 6.20 | 0.30 | 0.07 |
| 1:1 Mixture of 0 and 100 | 5 | 28 | 37 | 45.10 | 30.00 | 11.00 | 1.50 |
| 1:1 (0, 100) | 15 | 30 | 38 | 44.60 | 29.50 | 10.90 | 1.50 |
| 1:1 (0, 100) | 30 | 31 | 39 | 45.50 | 29.50 | 10.90 | 1.60 |
| 1:1 (0, 100) | 60 | 29 | 38 | 45.90 | 29.50 | 10.80 | 1.60 |
| 1:1 (0, 100) | 1015 | 31 | 38 | 45.10 | 29.50 | 10.80 | 1.60 |

TABLE 4

Effect of Ion Exchange on Cation Content and
$T_G$ and $T_M$ of "Neutral Iota Carrageenan"

| Ion Exchange Material g/l of 2% solution | Time Min | $T_G$ °C. | $T_M$ °C | Na mg/g | K mg/g | Ca mg/g | Mg mg/g |
|---|---|---|---|---|---|---|---|
| 0 | 0 | 25 | 38 | 22.00 | 53.90 | 6.30 | 7.40 |
| 50 | 30 | 10 | 19 | 64.30 | 19.40 | 0.20 | 0.22 |
| 100 | 30 | 5 | 17 | 69.60 | 12.30 | 0.10 | 0.12 |
| 200 | 30 | 5 | 17 | 73.40 | 6.30 | 0.08 | 0.07 |
| 1:1 Mixture of 0 and 100 | 5 | 14 | 23 | 45.20 | 32.60 | 3.40 | 3.90 |
| 1:1 (0, 100) | 15 | 12 | 20 | 45.90 | 33.10 | 3.40 | 3.90 |
| 1:1 (0, 100) | 30 | 14 | 23 | 44.80 | 32.30 | 3.40 | 3.80 |
| 1:1 (0, 100) | 60 | 12 | 20 | 46.00 | 33.10 | 3.40 | 3.90 |
| 1:1 (0, 100) | 1015 | 12 | 20 | 45.40 | 33.30 | 3.60 | 4.00 |

Figure 7:
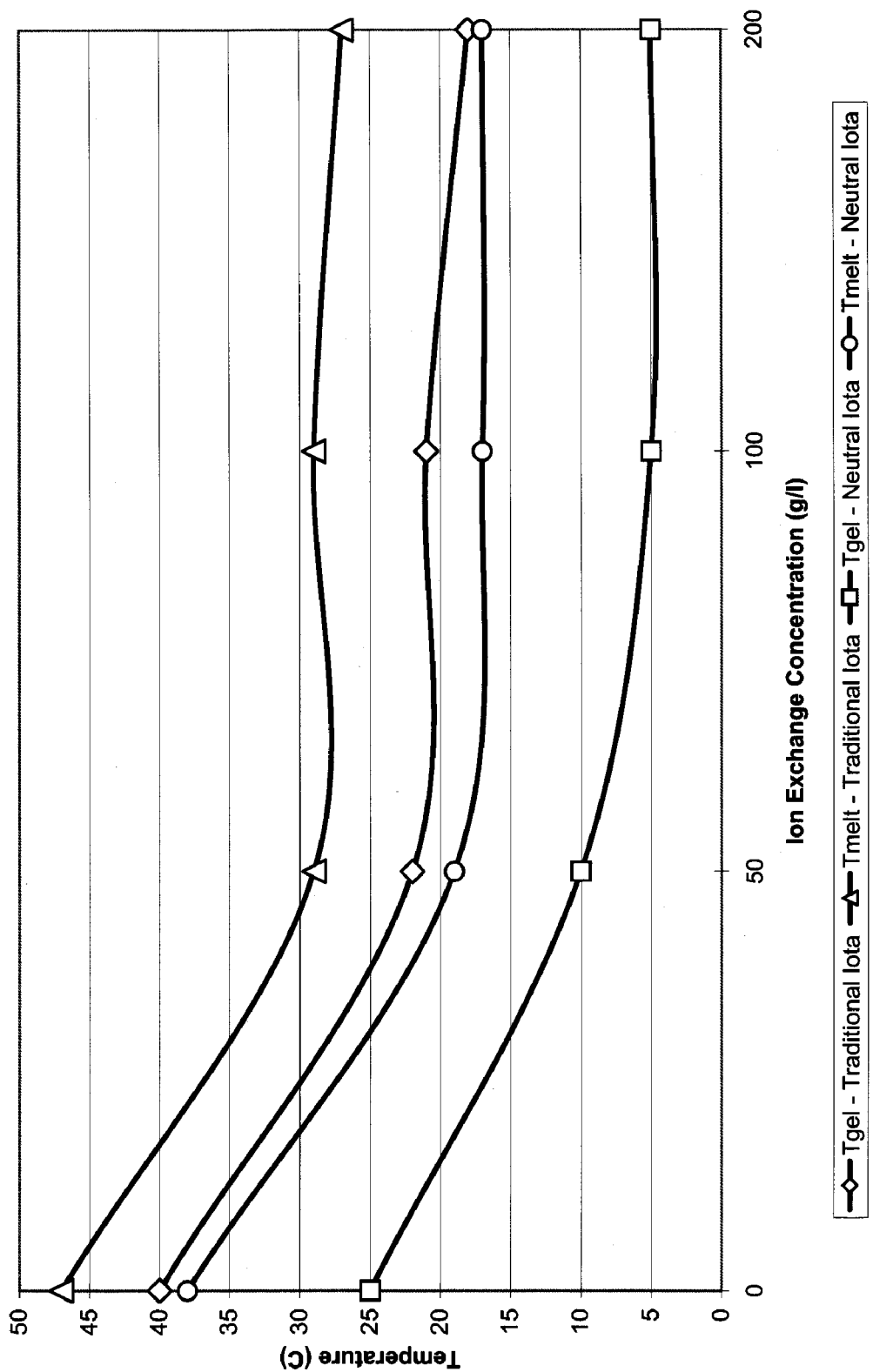
FIG. 7 shows the effect of ion exchange material concentration on gelling and melting temperatures of iota carrageenan.

As can be seen in the above tables and in FIG. 7, by contacting the iota carrageenan samples with the sodium form acidic cationic ion exchange material, gels made with traditional and neutral iota carrageenan had reduced $T_G$ and $T_M$. In addition, the $T_G$ and $T_M$ decreased as the ion-exchange concentration increased, eventually leveling off as the concentration approached 200 g/l (10 g/g carrageenan). For traditional iota carrageenan samples, the $T_G$ for the ion-exchanged samples ranged from about 18° C. to about 30° C., and the $T_M$ ranged from about 27° C. to about 37° C. For the neutrally extracted iota carrageenan samples, the $T_G$ for the ion-exchanged samples ranged from about 5° C. to about 17° C., and the $T_M$ ranged from about 17° C. to about 27° C.

Figure 8:
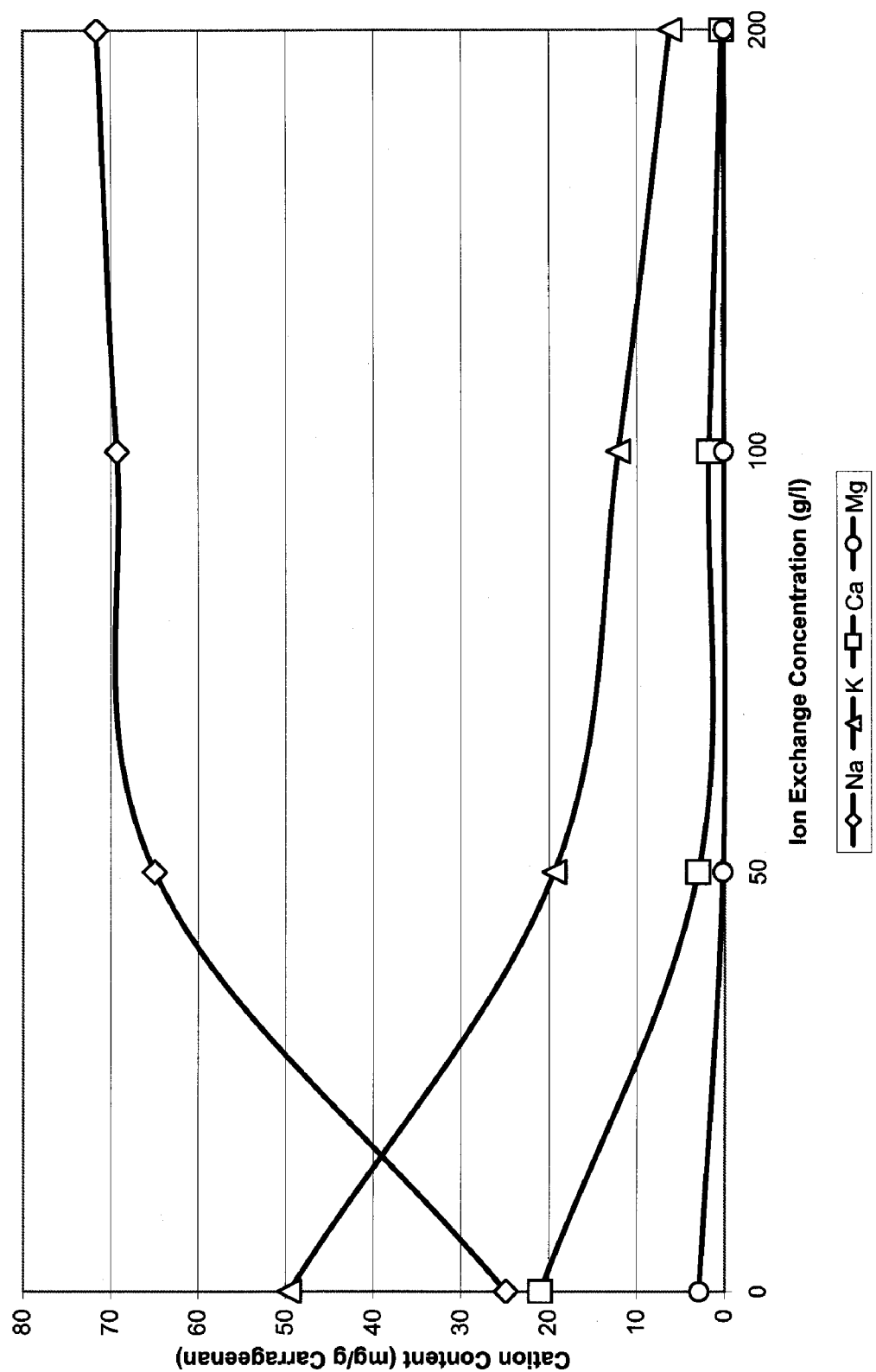
FIG. 8 shows the effect of ion exchange material concentration on cation composition of traditional iota carrageenan.
Figure 9:
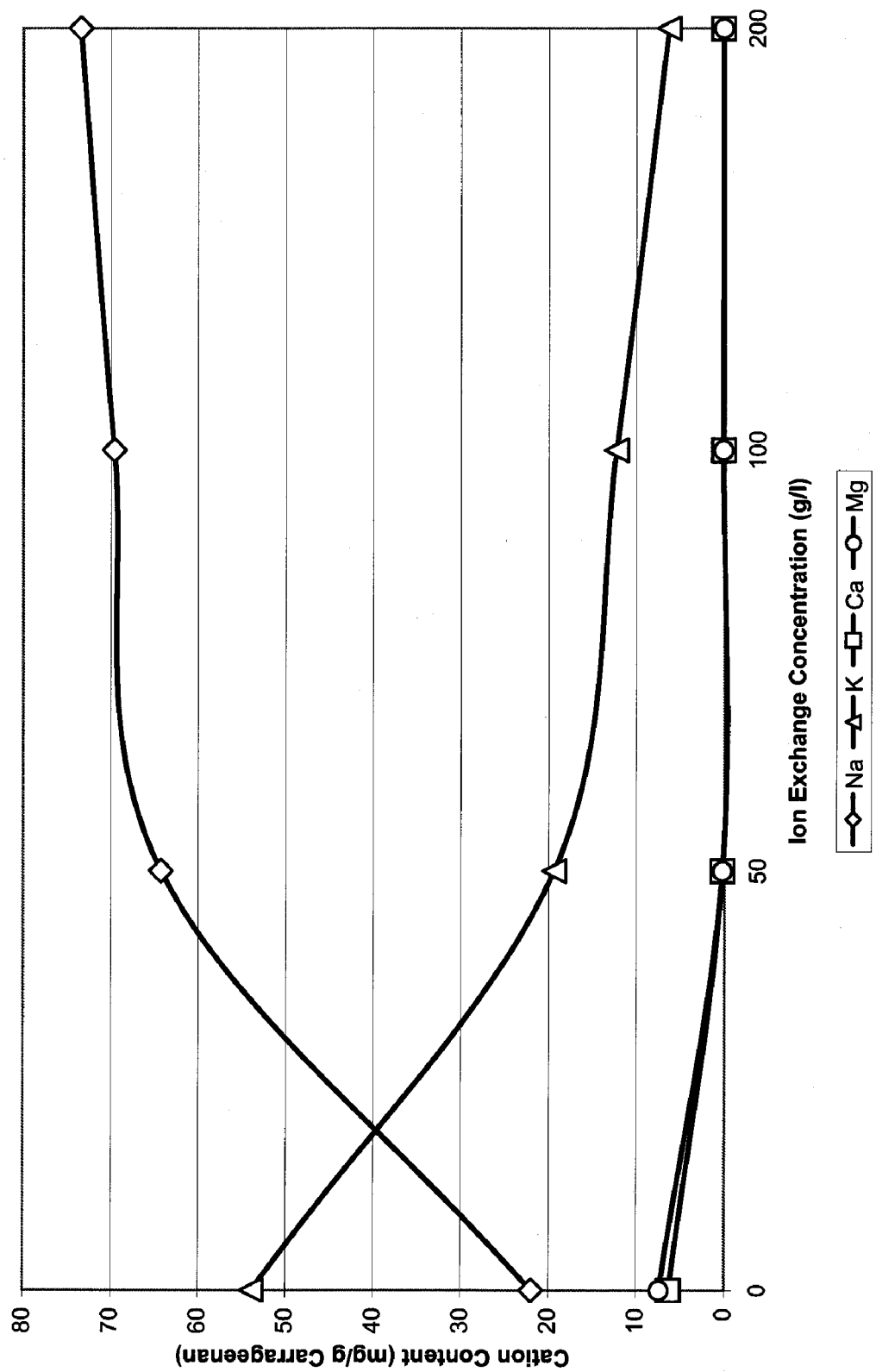
FIG. 9 shows the effect of ion exchange material concentration on cation composition of neutral iota carrageenan.

As can be seen in the above tables and in FIGS. 8 and 9, by contacting the iota carrageenan samples with the sodium form acidic cationic ion exchange material, the gelling cation content of the carrageenan was reduced. With the exception of the sodium ions, the levels of each of the cations decreased as the concentration of the ion exchange material increased. In contrast, the sodium levels increased with ion-exchange, as expected for a sodium form ion exchange resin. For the traditional iota carrageenan samples, the Potassium content of the ion-exchanged samples ranged between 6 and 35 mg/g, the Calcium content of the ion-exchanged samples ranged between 0 and 13 mg/g, and the Magnesium content of the ion-exchanged samples ranged between 0 and 2 mg/g. For the neutral iota carrageenan samples, the Potassium content of the ion-exchanged samples ranged between 6 and 35 mg/g, the Calcium content of the ion-exchanged samples ranged between 0 and 5 mg/g, and the Magnesium content of the ion-exchanged samples ranged between 0 and 5 mg/g. For all samples, the cation content eventually leveled off at about a 70 g/l concentration (based on interpolation of the data). In other words, for traditionally or neutrally extracted iota carrageenan, the lowest level of gelling cations could be achieved with an ion exchange concentration of 70 g/l (3.5 g/g carrageenan) or higher.

Comparing the traditional iota carrageenan data in Table 3 and FIGS. 7 and 8, of all of the gelling cations, potassium content was the most strongly correlated to the magnitude of the gelling and melting temperatures, particularly when the ion exchange concentration is higher than about 50 g/l (2.5 g/g carrageenan). Likewise, when comparing the neutral iota carrageenan data in Table 4 and FIGS. 7 and 9, potassium content was the most strongly correlated to the magnitude of the gelling and melting temperatures, particularly when the ion exchange concentration is higher than about 50 g/l (2.5 g/g carrageenan).

Example 4

Mixtures of Iota Carrageenans

Mixtures were prepared for both traditional and neutral iota carrageenans as follow. A carrageenan mixture was prepared by mixing a non-ion-exchanged iota carrageenan (indicated as 0 g/l) in a 1:1 ratio with a iota carrageenan that was ion exchanged with 100 g/l sodium form acidic cationic ion exchange resin (5 g/g carrageenan). The mixtures were made at 70° C., and allowed to stand at 70° C. while stirring from 5 minutes to about 1000 minutes, with samples taken periodically during the mixing process. Each of the sample solutions was precipitated in three volumes 100% isopropyl alcohol, dried over night at 70° C. and milled on 0.250 mm sieve. Gelling ion content, $T_G$, and $T_M$ were measured for each mixture sample. The results are set forth in Tables 3 and 4, above, as well as in FIGS. 10-12.

Figure 10:
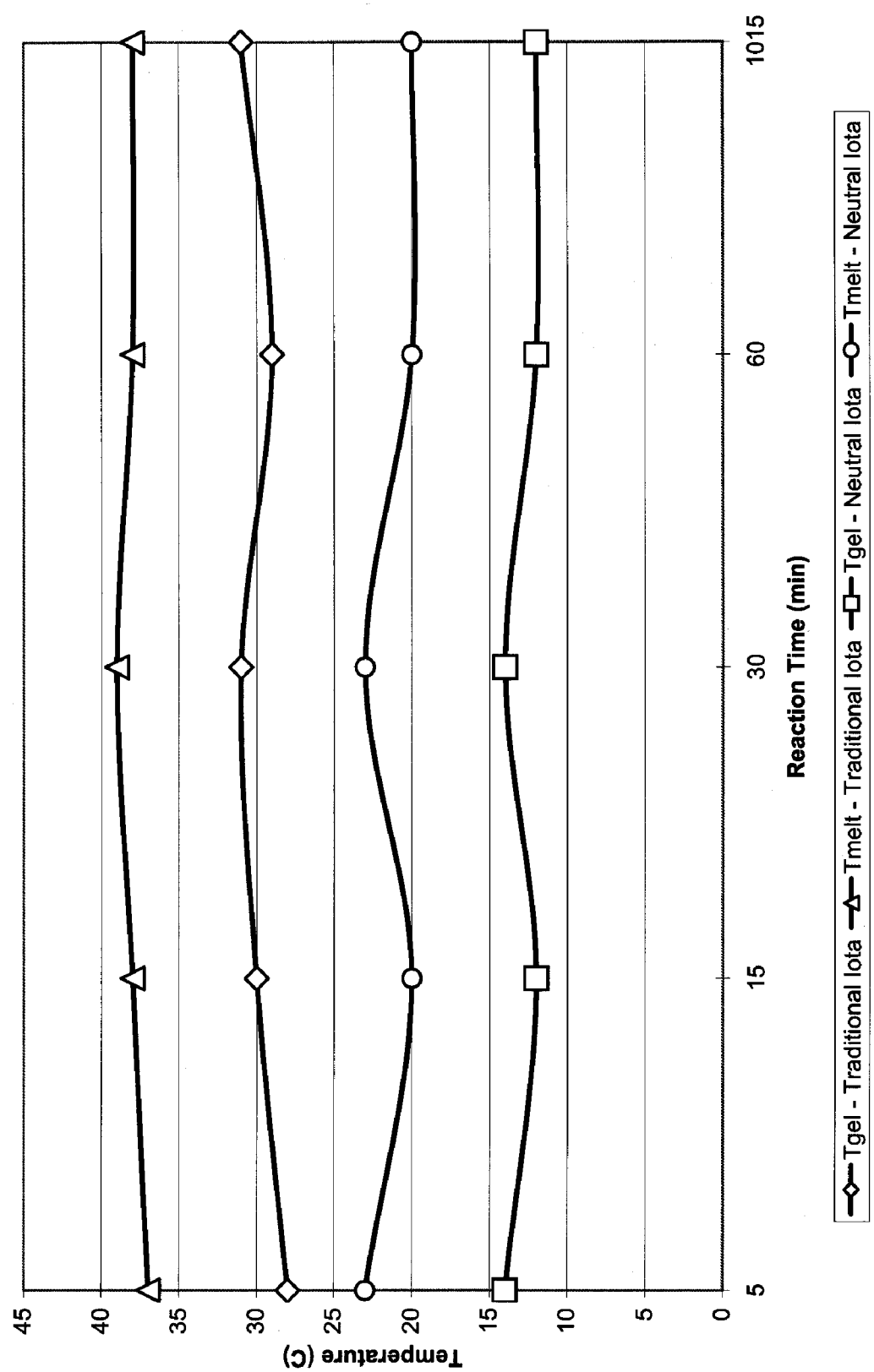
FIG. 10 shows the gelling and melting temperatures of a mixture of a non-ion exchanged iota carrageenan extract and an iota carrageenan extract having been ion exchanged using 100 g ion exchange material per liter extract.
Figure 11:
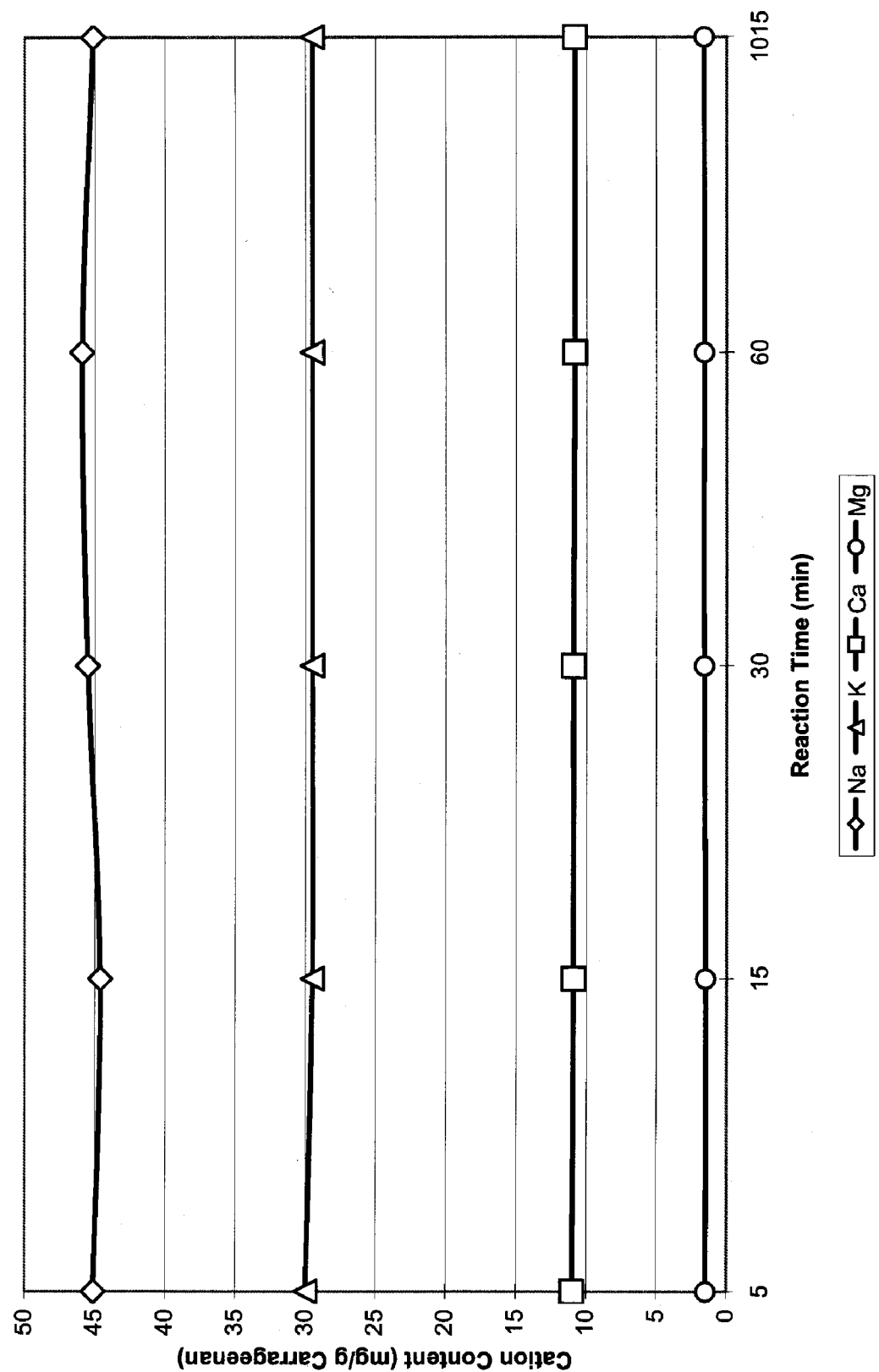
FIG. 11 shows the cation composition of a 1:1 mixture of traditional non-ion exchanged iota carrageenan and traditional ion exchanged iota carrageenan.
Figure 12:
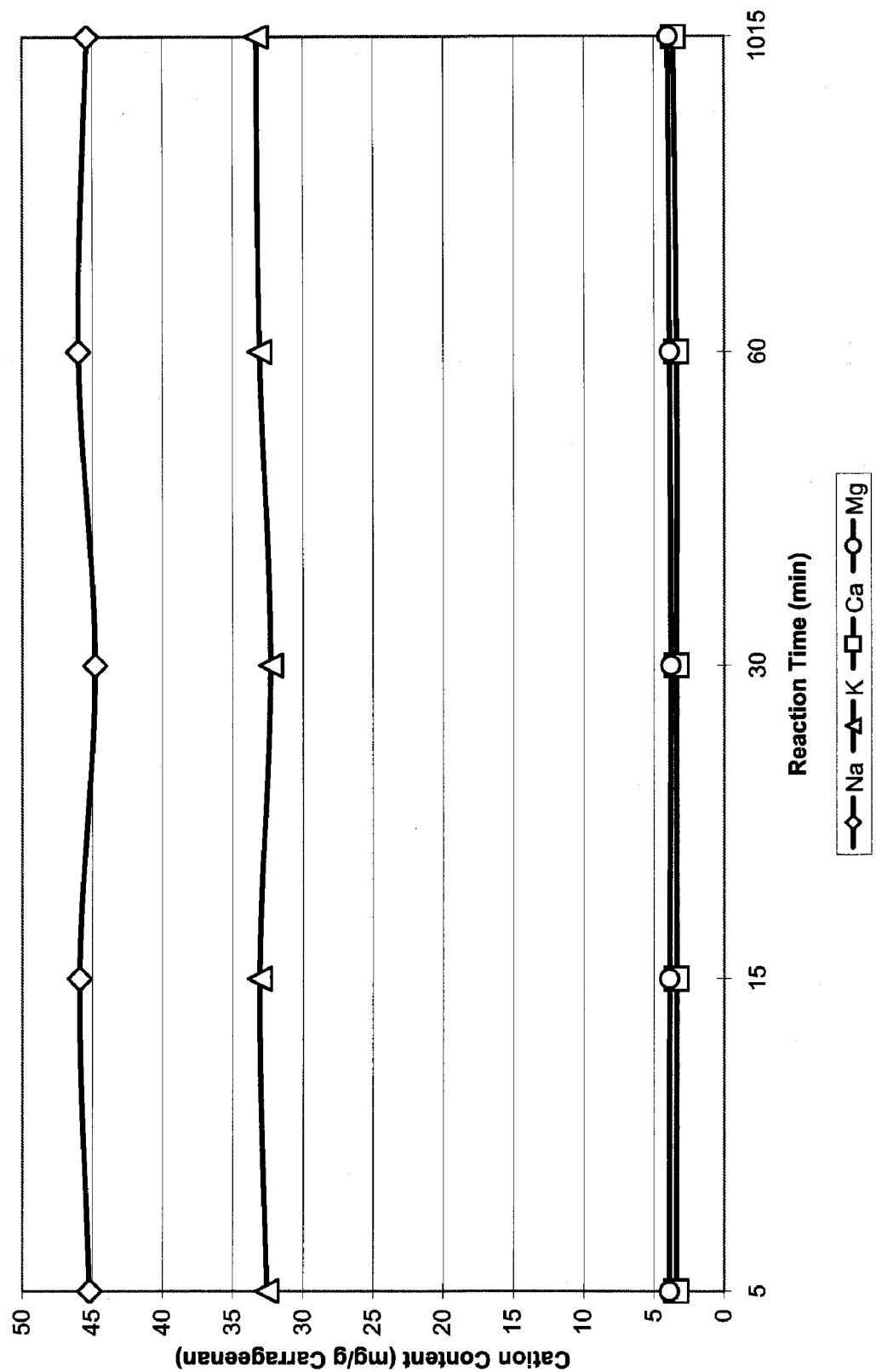
FIG. 12 shows the cation composition of a 1:1 mixture of neutral extracted non-ion exchanged iota carrageenan and neutral extracted ion exchanged iota carrageenan.

FIGS. 10-12 show the results of mixing a non-ion-exchanged iota carrageenan with an ion-exchanged iota carrageenan. FIG. 10 shows the $T_G$ and $T_M$ over time for a 1:1 mixture of non-ion-exchanged iota carrageenan extract with iota carrageenan extract that was ion exchanged at an ion exchange resin concentration of 100 g/l ion exchange resin (both traditional and neutral iota carrageenans). As can be seen in FIG. 10 within 15 minutes of mixing the two carrageenan fractions, the $T_G$ and $T_M$ of the mixture was approximately the mid-point of the $T_G$ and $T_M$ of the respective individual iota carrageenan fractions.

FIG. 11 shows the gelling cation composition over time for a 1:1 mixture of non-ion-exchanged traditional iota carrageenan extract with traditional iota carrageenan extract that was ion exchanged at an ion exchange resin concentration of 100 g/l. FIG. 12 shows the gelling cation composition over time for a 1:1 mixture of non-ion-exchanged neutral iota carrageenan extract with neutral iota carrageenan extract that was ion exchanged at an ion exchange resin concentration of 100 g/l. Here, the data shows that almost immediately upon mixing the two carrageenan fractions, the cation composition of the resulting mixture was approximately the mid-point of the cation composition of the respective individual iota carrageenan fractions.

The previous examples illustrate several aspects of carrageenan production in an ion exchange process. However, the time during which the two fractions of carrageenan have been in contact in dissolved form, was not closely controlled. During the preparation of the combined fractions, the contact time was controlled, but the contact time during preparation of the air gel samples, the contact time during cooling and the contact time before the air gel samples were measured, were not specifically controlled and have varied from a few hours to several days. Thus, it was not determined how fast the ions in the two carrageenan fractions found equilibrium on the molecular level.

Example 5

Mixtures of Traditional Iota Carrageenans

In this experiment, two "traditional iota carrageenan" fractions were made up to form individual air gel preparations at 70° C. One fraction was not ion exchanged whereas the other fraction was ion exchanged with 100 g/l sodium form acidic cationic ion exchange material (5 g/g carrageenan). These separate air gel preparations were then mixed at 60° C. and immediately transferred to the rheometer and measured. The time elapsing from mixing the two air gel fractions and to the measurement started was less than 5 minutes. The results are set forth, in Table 5 below and in FIG. 14.

TABLE 5

Effect of Mixture Ratio on $T_G$ and $T_M$ of Traditional Iota Carrageenan Mixture

| % Ion Exchanged Carrageenan (100 g/l) | % Non-Ion-Exchanged Carrageenan (0 g/l) | $T_G$ °C. | $T_M$ °C. |
|---|---|---|---|
| 0 | 100 | 40 | 47 |
| 25 | 75 | 34 | 42 |
| 50 | 50 | 28 | 36 |
| 75 | 25 | 25 | 33 |
| 100 | 0 | 21 | 29 |

Figure 14:
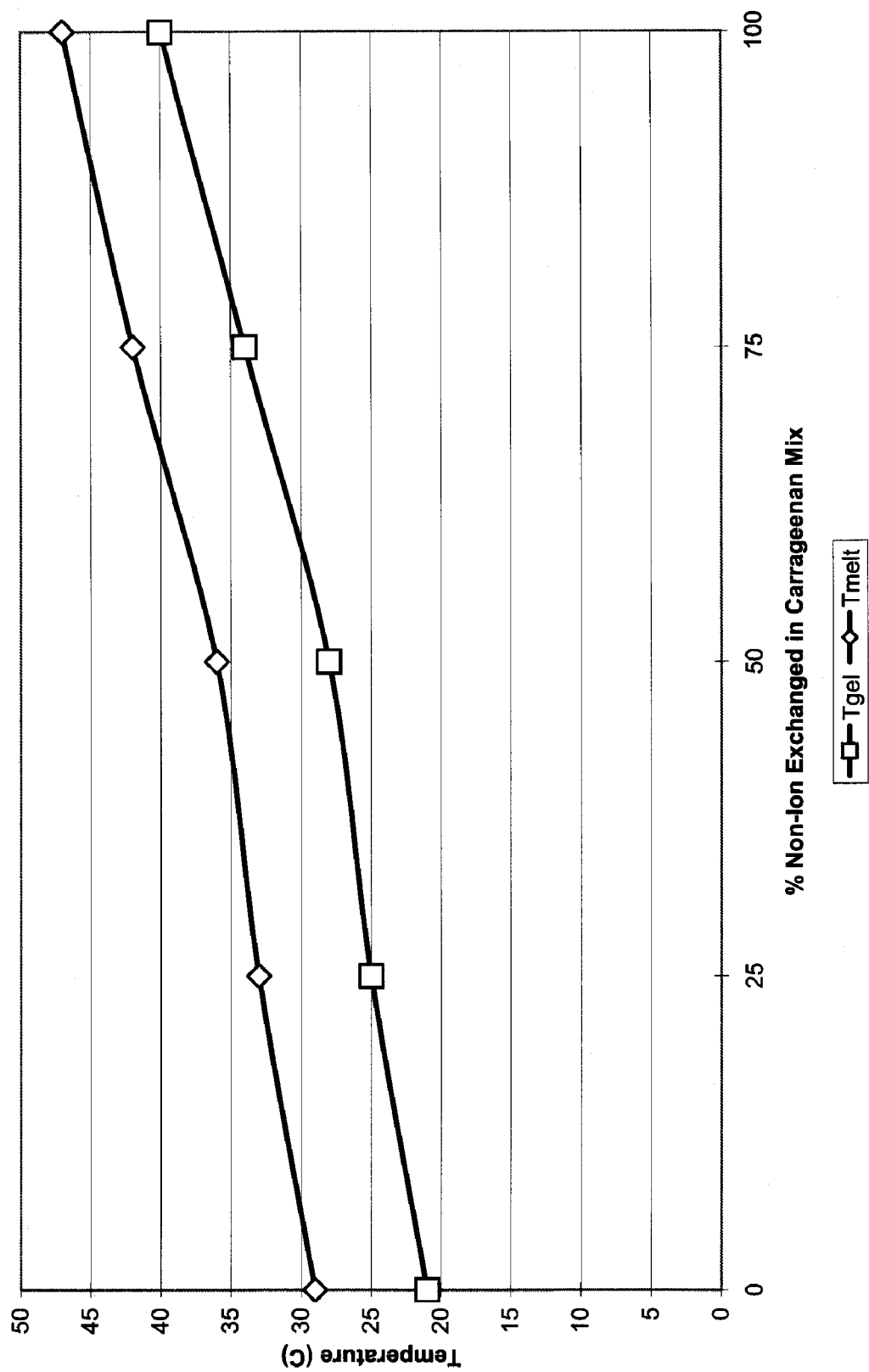
FIG. 14 shows the gelling and melting temperatures of traditional iota carrageenan mixtures.

As can be seen from the above data and FIG. 14, for mixtures of ion-exchanged and non-ion-exchanged traditional iota carrageenan, there is a linear relation between the concentration of the individual carrageenan fractions and the gelling and melting temperatures. At a ratio of 1:1, the gelling and melting temperatures are identical to those in Table 3.

Example 6

Mixtures of Dry Iota Carrageenans in Water and Oil

Figure 15:
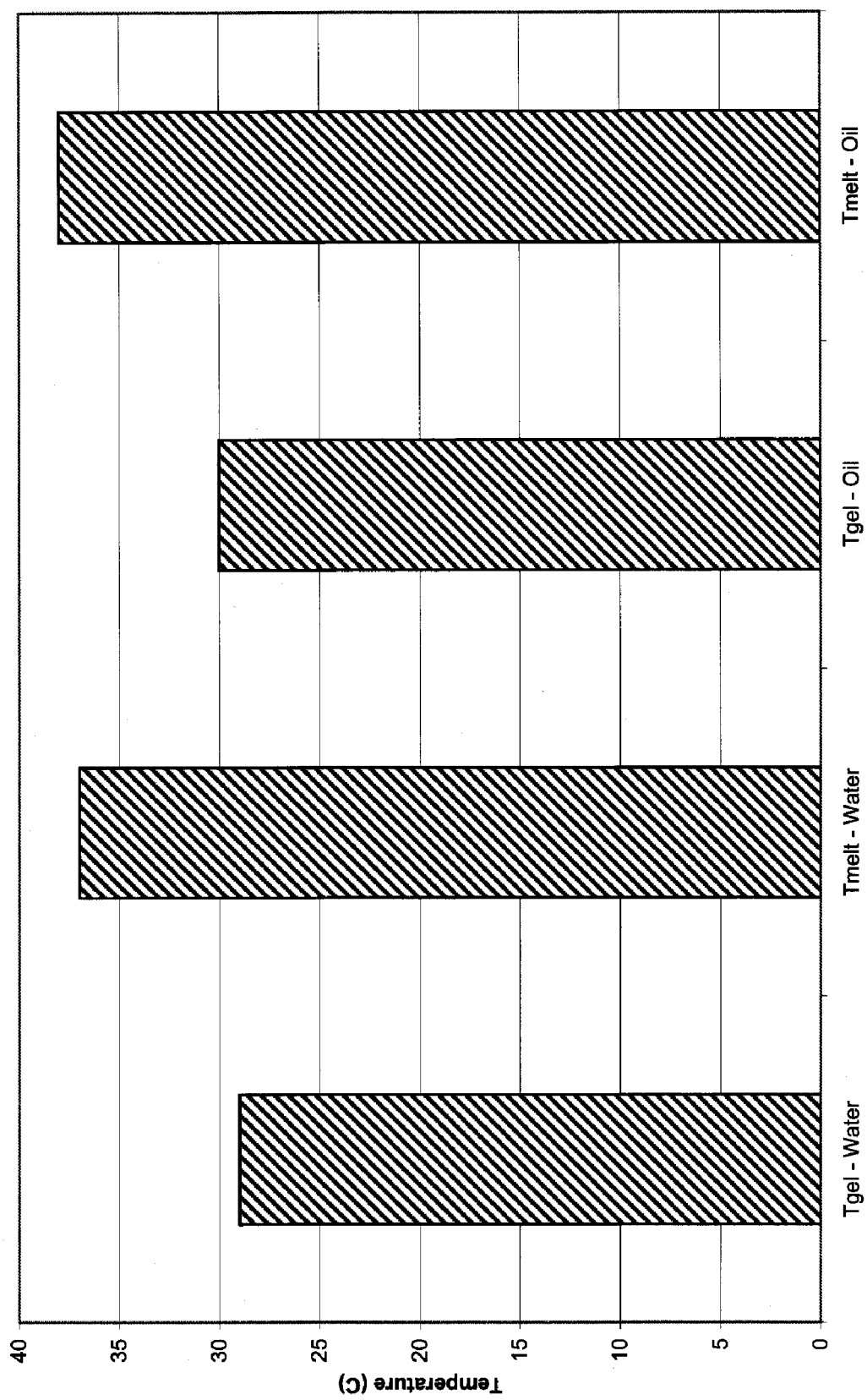
FIG. 15 shows the gelling and melting temperatures of a dry mixture of non-ion exchanged and ion exchanged tradition iota carrageenan products.

In the following experiment, dry mixes of the same two traditional iota carrageenan fractions as used to generate the results Example 5 were mixed and combined with water and oil, as follows. In the first sample, 0.12 g of the non-ion exchanged material was mixed with 0.12 g of the ion-exchanged material and dispersed in a water phase. As soon as the material was properly dispersed, the dispersion was heated to 70° C., cooled to 60° C. and added to a 50° C. hot oil phase. During the heating, it was observed that thinning out took place at about 35-40° C. The mixture was cooled to 45° C. and immediately poured into the rheometer. The time from the start of the dispersion to the start of measurement was 16 minutes. The $T_G$ and $T_M$ for the first sample are shown graphically in FIG. 15.

In the second sample, 0.12 g of the non-ion exchanged material was mixed with 0.12 g of the ion-exchanged material and dispersed in an oil phase at 50° C. A 70° C. hot water phase was then added to the oil phase, and mixed for 1 minute. The sample was immediately transferred to the rheometer. The time from dispersion to the start of the measurement was 5 minutes. The $T_G$ and $T_M$ for the second sample are shown graphically in FIG. 15.

The results demonstrate that one can dry mix carrageenan fractions having different $T_G$ and $T_M$, and still obtain the same result, i.e., obtain a carrageenan gel having $T_G$ and $T_M$ that are between the $T_G$ and $T_M$ of the individual carrageenan fractions. In this example, after mixing dry fractions of iota carrageenan and dissolving such dry mixes in the water phase or first dispersing such dry mixes in the oil phase, the $T_G$ and $T_M$ of the resulting gel fell between the $T_G$ and $T_M$ of the individual carrageenan fractions. Dry mixing of the carrageenans is beneficial because it may be easier to provide customized dry mixtures of carrageenan fractions.

Example 7

Ion Exchange of Seaweed Extract

In the above examples, the ion exchange took place on dissolved carrageenan. However, in commercial production, the ion exchange typically would take place on a carrageenan extract from seaweed. In this example, a neutral kappa carrageenan seaweed extract was prepared and subjected to the ion exchange process, according to the method described above. Compared to the experiments using dissolved carrageenan, the experiments with seaweed extract used water and alcohol from the production plant. Both the water and the alcohol from the plant typically contain more cations than demineralized water from the laboratory and unrectified alcohol.

The gelling cation contents were measured for these neutrally extracted kappa carrageenan samples. The results for samples precipitated using 80% and 100% isopropyl alcohol (from the plant) are shown in Table 6 below, and in FIG. 16.

TABLE 6

Effect of Ion Exchange on Neutrally Extracted Kappa Carrageenan Seaweed Extract

| Sample | % IPA in precipitation | Ion Exchange Material g/l of 2% solution | K Mg/g | Na Mg/g | Ca Mg/g | Mg Mg/g |
|---|---|---|---|---|---|---|
| 1 | 80 | 0 | 35.8 | 19.7 | 3.3 | 6.2 |
| 2 | 80 | 100 | 8.2 | 51.7 | 0.15 | 0.13 |
| 3 | 80 | 150 | 5.6 | 53.1 | 0.08 | 0.08 |
| 4 | 100 | 0 | 37 | 21.5 | 3.2 | 6 |
| 5 | 100 | 100 | 7.7 | 55.2 | 0.12 | 0.1 |
| 6 | 100 | 150 | 5 | 56.2 | 0.03 | 0.07 |

As an initial matter, the results show that the non-ion-exchanged neutrally extracted kappa carrageenan from seaweed extract had a higher cation content than that of the neutral kappa carrageenan samples made with dissolved carrageenan. Without intending to be bound by theory, it is believed that this is due, at least in part, to a higher load of cations in the water and alcohol used in commercial production. The sodium and potassium levels for the samples precipitated with 100% IPA were slightly higher than the sodium and potassium levels for samples precipitated with 80% IPA.

Figure 16:
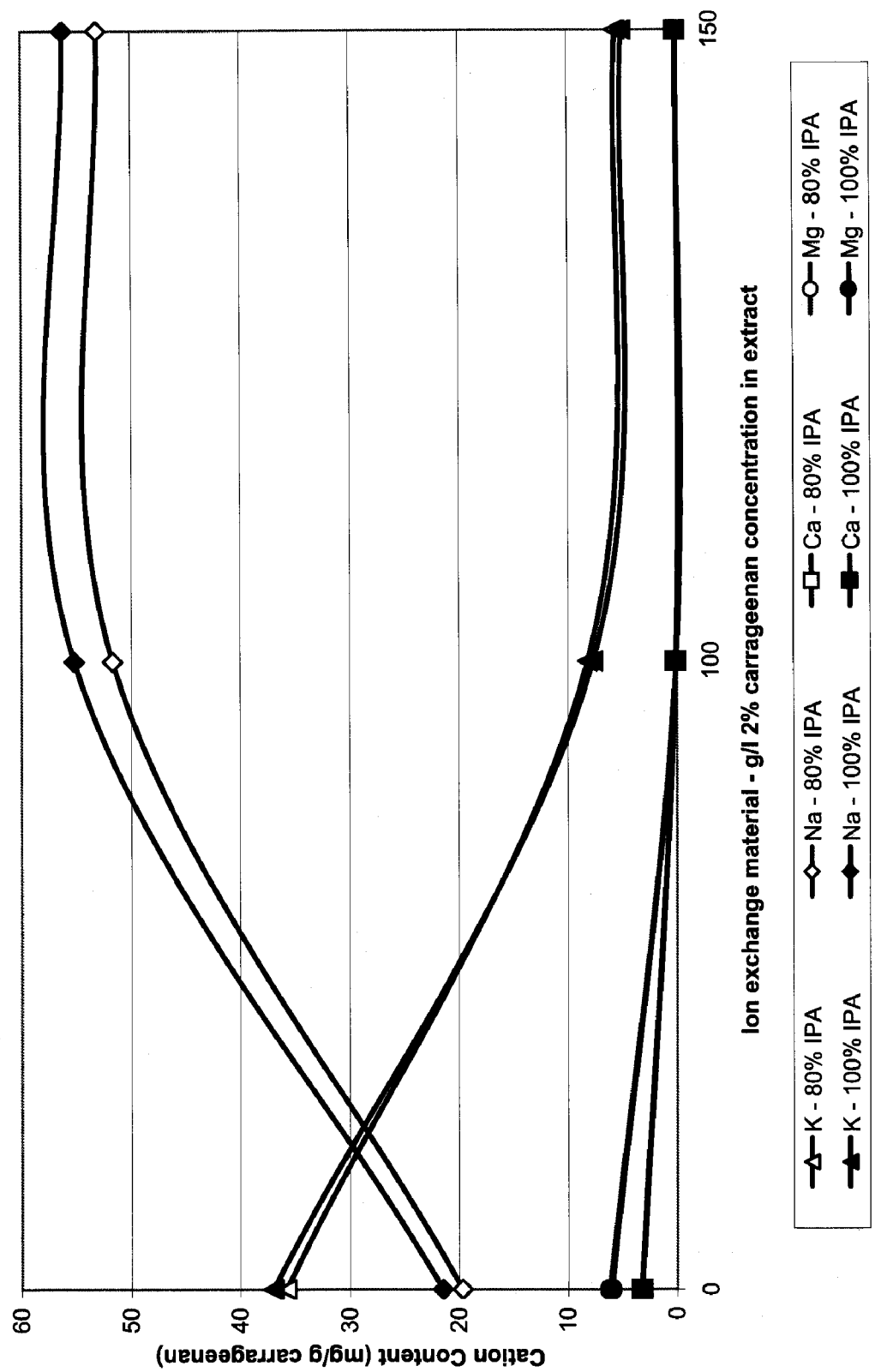
FIG. 16 shows the effect of ion exchange resin concentration and precipitating alcohol concentration on cation levels in kappa carrageenan systems.

As can be seen in Table 6 and FIG. 16, by contacting the neutrally extracted kappa carrageenan with the sodium form acidic cationic ion exchange material, the gelling cation content of the carrageenan was reduced (similar to result observed with the dissolved carrageenan). With the exception of the sodium ions, the levels of each of the cations decreased as the concentration of the ion exchange material increased. In contrast, the sodium levels increased with increased concentration of ion exchange material, as expected for a sodium form ion exchange resin. In addition, the gelling cation content at different amounts of ion exchange material and at different alcohol percentages during precipitation.

This example shows that when ion-exchanging an extract of carrageenan, the amount of ion exchange material may have to be increased as compared to that necessary for dissolved carrageenan. By interpolating the data in FIG. 16, it appears that the potassium content leveled out at a minimum content at an ion exchange concentration of about 120 g/l (for a 2% solution, or 6 g/g carrageenan). It appears that the calcium and magnesium content leveled out at a minimum content at an ion-exchange concentration of about 100 g/l (5 g/g carrageenan). It appears that the sodium content leveled out at a maximum content at about 120 g/l (6 g/g carrageenan). In comparison, for the dissolved neutral kappa carrageenan samples in Example 1, the gelling cation composition leveled off at an ion-exchange material concentration of about 70 g/l (3.5 g/g carrageenan). Without intending to be bound by any particular theory, this difference may be explained, in part, by the higher load of cations in the non-ion-exchanged extract and a higher load of cations in the water and alcohol used in commercial production.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the exemplary embodiments as defined by the appended claims.

What is claimed is:

1. A composition comprising an iota carrageenan that has been subjected to an ion exchange process, wherein the iota carrageenan comprises:
   a potassium content of about 6 mg/g to about 35 mg/g carrageenan;
   a calcium content of less than about 13 mg/g carrageenan; and
   a magnesium content of less than about 5 mg/g carrageenan.

2. The composition according to claim 1, wherein the iota carrageenan is traditionally-extracted carrageenan and has a gelling temperature of between about 18° C. to about 30° C., and a melting temperature of between about 27° C. to about 37° C.

3. The composition according to claim 1, wherein the iota carrageenan is neutral extracted carrageenan and has a gelling temperature of between about 5° C. to about 17° C., and a melting temperature of between about 17° C. to about 27° C.

4. A composition comprising a traditionally-extracted kappa carrageenan that has been subjected to an ion exchange process, wherein the kappa carrageenan comprises:
   a potassium content of about 5 mg/g to about 30 mg/g carrageenan;
   a calcium content of less than about 7 mg/g carrageenan; and
   a magnesium content of less than about 0.2 mg/g carrageenan.

5. A composition comprising a neutrally-extracted kappa carrageenan that has been subjected to an ion exchange process, wherein the kappa carrageenan comprises:
   a potassium content of about 4 mg/g to about 30 mg/g carrageenan;
   a calcium content of less than about 3 mg/g carrageenan; and
   a magnesium content of less than about 3 mg/g carrageenan.

6. The composition according to claim 4, wherein the carrageenan has a gelling temperature of between about 10° C. to about 27° C., and a melting temperature of between about 23° C. to about 43° C.

7. The composition according to claim 5, wherein the carrageenan has a gelling temperature of between about 10° C. to about 35° C., and a melting temperature of between about 23° C. to about 45° C.

8. A process for producing an ion-exchanged carrageenan composition, comprising the steps of: extracting a carrageenan starting material with an aqueous treatment solution to form an iota carrageenan extract; contacting the iota carrageenan extract with an acidic cationic ion-exchange material and reducing the cation content of the iota carrageenan extract to produce an ion-exchanged iota carrageenan extract, wherein the ion exchanged iota carrageenan extract has a potassium content of about 6 mg/g to about 35 mg/g carrageenan; a calcium content of less than about 13 mg/g carrageenan; and a magnesium content of less than about 5 mg/g carrageenan.

9. A process for producing an ion-exchanged carrageenan composition, comprising the steps of: neutrally extracting a carrageenan starting material with an aqueous treatment solution to form a neutral kappa carrageenan extract; contacting the neutral kappa carrageenan extract with an acidic cationic ion-exchange material and reducing the cation content of the neutral kappa carrageenan extract to produce an ion-exchanged neutral kappa carrageenan extract, wherein the ion-exchanged neutral kappa carrageenan extract has a potassium content of about 4 mg/g to about 30 mg/g carrageenan; a calcium content of less than about 3 mg/g carrageenan; and a magnesium content of less than about 3 mg/g carrageenan.

10. A process for producing an ion-exchanged carrageenan composition, comprising the steps of: traditionally extracting a carrageenan starting material with an aqueous treatment solution to form a traditional kappa carrageenan extract; contacting the traditional kappa carrageenan extract with an acidic cationic ion-exchange material and reducing the cation content of the traditional kappa carrageenan extract to produce an ion-exchanged traditional kappa carrageenan extract, wherein the ion-exchanged traditional kappa carrageenan extract has a potassium content of about 5 mg/g to about 30 mg/g carrageenan; a calcium content of less than about 7 mg/g carrageenan; and a magnesium content of less than about 0.2 mg/g carrageenan.

* * * * *

UNITED STATES PATENT AND TRADEMARK OFFICE
CERTIFICATE OF CORRECTION

Page 1 of 1

PATENT NO.       : 8,293,285 B2
APPLICATION NO.  : 12/403097
DATED            : October 23, 2012
INVENTOR(S)      : Trudsoe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 286 days.

Signed and Sealed this
Twentieth Day of November, 2012

David J. Kappos
*Director of the United States Patent and Trademark Office*